US010799567B2

(12) United States Patent
Bellgrau et al.

(10) Patent No.: US 10,799,567 B2
(45) Date of Patent: Oct. 13, 2020

(54) YEAST-BASED IMMUNOTHERAPY AND TYPE I INTERFERON SENSITIVITY

(71) Applicants: GLOBEIMMUNE, INC., Louisville, CO (US); THE REGENTS OF THE UNIVERSITY OF COLORADO, Denver, CO (US)

(72) Inventors: Donald Bellgrau, Highlands Ranch, CO (US); Thomas H. King, Denver, CO (US)

(73) Assignees: GlobeImmune, Inc., Louisville, CO (US); The Regents of the University of Coloradio, Denver, CO (US)

( * ) Notice: Subject to any disclaimer, the term of this patent is extended or adjusted under 35 U.S.C. 154(b) by 0 days.

(21) Appl. No.: 15/303,434

(22) PCT Filed: Apr. 10, 2015

(86) PCT No.: PCT/US2015/025316

§ 371 (c)(1),
(2) Date: Oct. 11, 2016

(87) PCT Pub. No.: WO2015/157639

PCT Pub. Date: Oct. 15, 2015

(65) Prior Publication Data

US 2017/0035867 A1 Feb. 9, 2017

Related U.S. Application Data

(60) Provisional application No. 61/978,634, filed on Apr. 11, 2014.

(51) Int. Cl.

| | |
|---|---|
| ***A61K 39/00*** | (2006.01) |
| ***A61K 36/064*** | (2006.01) |
| ***G01N 33/573*** | (2006.01) |

(52) U.S. Cl.

CPC ........ *A61K 39/0011* (2013.01); *A61K 36/064* (2013.01); *G01N 33/573* (2013.01); *A61K 2039/52* (2013.01); *A61K 2039/57* (2013.01); *G01N 2333/555* (2013.01); *G01N 2333/914* (2013.01); *G01N 2800/52* (2013.01)

(58) Field of Classification Search

None

See application file for complete search history.

(56) References Cited

U.S. PATENT DOCUMENTS 4,775,622 A 10/1988 Hitzeman et al.
5,234,830 A 8/1993 Oshima et al.
5,310,654 A 5/1994 Isberg et al.
5,413,914 A 5/1995 Franzusoff
5,830,463 A 11/1998 Duke et al.
5,858,378 A 1/1999 Bostwick
5,919,651 A 7/1999 Hitzeman et al.
7,083,787 B2 * 8/2006 Duke .................... A61K 39/00 424/184.1
7,439,042 B2 10/2008 Duke et al.
7,465,454 B2 * 12/2008 Franzusoff ......... A61K 39/0011 424/191.1
7,563,447 B2 * 7/2009 Franzusoff ......... A61K 39/0011 424/191.1
7,595,060 B2 9/2009 Duke et al.
7,625,569 B2 * 12/2009 Duke .................... A61K 39/29 424/192.1
7,632,511 B2 * 12/2009 Duke .................... A61K 39/29 424/192.1
7,736,642 B2 * 6/2010 Duke .................. A61K 39/145 424/184.1
7,745,128 B2 * 6/2010 Guo .................. A61K 39/0011 435/6.14
8,007,816 B2 * 8/2011 Duke .................... A61K 39/29 424/192.1
8,067,559 B2 * 11/2011 Franzusoff ......... A61K 39/0011 536/23.1
8,153,136 B2 * 4/2012 Franzusoff ......... A61K 39/0011 424/184.1
8,337,830 B2 * 12/2012 Franzusoff ......... A61K 39/0011 424/93.2
8,343,502 B2 * 1/2013 Franzusoff ......... A61K 39/0011 424/185.1

(Continued)

FOREIGN PATENT DOCUMENTS

CN 101195844 6/2008
CN 101479389 7/2009

(Continued)

OTHER PUBLICATIONS

Bui et al, Mutation-specific control of BCR-ABL T3151positive leukemia with a recombinant yeast-based therapeutic vaccine in a murine model. Vaccine, 28 (2010) 6028-6035 Available online Jul. 7, 2010 (Year: 2010).*

(Continued)

*Primary Examiner* — Nita M. Minnifield

(74) *Attorney, Agent, or Firm* — Sheridan Ross P.C.

(57) ABSTRACT

Disclosed are methods of treating individuals with yeast-based immunotherapy who have been preselected as being sensitive to type I interferons, as well as methods for selecting individuals for treatment with yeast-based immunotherapeutic compositions and methods for enhancing or improving an individual's response to yeast-based immunotherapy, based on the individual's sensitivity to type 1 interferons (T1IFNs).

12 Claims, 7 Drawing Sheets

Specification includes a Sequence Listing.

(56) References Cited

U.S. PATENT DOCUMENTS

| | | | | |
|---|---|---|---|---|
| 8,388,980 | B2 * | 3/2013 | Duke | A61K 39/29 424/192.1 |
| 8,734,778 | B2 * | 5/2014 | Franzusoff | A61K 39/0011 424/93.1 |
| 8,877,205 | B2 * | 11/2014 | Apelian | A61K 39/292 424/189.1 |
| 8,911,722 | B2 * | 12/2014 | Bellgrau | A61K 39/39541 424/184.1 |
| 9,198,941 | B2 * | 12/2015 | Palena | A61K 38/17 |
| 9,579,377 | B2 * | 2/2017 | King | A61K 39/29 |
| 9,623,097 | B2 * | 4/2017 | Palena | A61K 38/17 |
| 10,117,915 | B2 * | 11/2018 | Bellgrau | A61K 39/39541 |
| 10,188,714 | B2 * | 1/2019 | Franzusoff | C07K 14/4727 |
| 10,363,294 | B2 * | 7/2019 | Palena | A61K 39/0011 |
| 10,383,924 | B2 * | 8/2019 | Hodge | A61K 39/0011 |
| 2002/0044948 | A1 | 4/2002 | Samir et al. | |
| 2003/0035810 | A1 | 2/2003 | Caplan | |
| 2004/0156858 | A1 * | 8/2004 | Franzusoff | A61K 39/0011 424/185.1 |
| 2007/0172503 | A1 | 7/2007 | Selitrennikoff et al. | |
| 2007/0224208 | A1 * | 9/2007 | Guo | A61K 39/0011 424/184.1 |
| 2008/0003239 | A1 | 1/2008 | Duke et al. | |
| 2008/0069833 | A1 * | 3/2008 | Franzusoff | A61K 39/0011 424/190.1 |
| 2009/0069833 | A1 * | 3/2009 | Li | A61B 5/15002 606/182 |
| 2009/0074805 | A1 | 3/2009 | Duke et al. | |
| 2009/0098154 | A1 * | 4/2009 | Franzusoff | A61K 39/0011 424/192.1 |
| 2009/0142366 | A1 * | 6/2009 | Franzusoff | A61K 39/0011 424/185.1 |
| 2009/0142367 | A1 * | 6/2009 | Franzusoff | A61K 39/0011 424/192.1 |
| 2009/0304741 | A1 | 12/2009 | Duke et al. | |
| 2010/0034840 | A1 | 2/2010 | Apelian et al. | |
| 2010/0104604 | A1 | 4/2010 | Selitrennikoff et al. | |
| 2010/0111912 | A1 | 5/2010 | Apelian et al. | |
| 2010/0150963 | A1 | 6/2010 | Duke et al. | |
| 2010/0189749 | A1 | 7/2010 | Franzusoff et al. | |
| 2010/0196411 | A1 | 8/2010 | Duke et al. | |
| 2010/0215678 | A1 | 8/2010 | Guo et al. | |
| 2011/0150909 | A1 * | 6/2011 | Franzusoff | A61K 39/0011 424/185.1 |
| 2011/0256098 | A1 | 10/2011 | Apelian et al. | |
| 2012/0107347 | A1 | 5/2012 | Hodge et al. | |
| 2012/0321664 | A1 | 12/2012 | Bellgrau et al. | |
| 2013/0071420 | A1 * | 3/2013 | Franzusoff | A61K 39/0011 424/188.1 |
| 2013/0149340 | A1 * | 6/2013 | Franzusoff | A61K 39/0011 424/274.1 |
| 2014/0193362 | A1 * | 7/2014 | King | A61K 39/29 424/85.4 |
| 2014/0302098 | A1 * | 10/2014 | Franzusoff | A61K 39/0011 424/277.1 |
| 2014/0308305 | A1 * | 10/2014 | Franzusoff | A61K 39/0011 424/185.1 |
| 2016/0106824 | A1 * | 4/2016 | Palena | A61K 38/17 424/185.1 |
| 2017/0035867 | A1 * | 2/2017 | Bellgrau | A61K 36/064 |
| 2017/0182153 | A1 * | 6/2017 | King | A61K 39/29 |
| 2018/0214525 | A1 * | 8/2018 | King | A61K 39/0011 |
| 2019/0022197 | A1 * | 1/2019 | Bellgrau | A61K 39/0005 |
| 2019/0035867 | A1 * | 1/2019 | Choung | H01L 27/3246 |
| 2019/0231859 | A1 * | 8/2019 | Franzusoff | A61K 39/0002 |

FOREIGN PATENT DOCUMENTS

| | | | |
|---|---|---|---|
| CN | 101594882 | 12/2009 | |
| CN | 101750474 | 6/2010 | |
| CN | 102197143 | 9/2011 | |
| EP | 0414404 | 2/1991 | |
| FR | 2486400 | 1/1982 | |
| WO | WO 2010/065626 | 6/2010 | |
| WO | WO-2011032119 A1 * | 3/2011 | A61K 39/39541 |
| WO | WO 2011/115914 | 9/2011 | |
| WO | WO 2012/019127 | 2/2012 | |
| WO | WO 2012/083302 | 6/2012 | |
| WO | WO 2012/109404 | 8/2012 | |
| WO | WO 2012/125998 | 9/2012 | |
| WO | WO 2012/174220 | 12/2012 | |
| WO | WO-2012174220 A1 * | 12/2012 | A61K 39/29 |
| WO | WO 2013/025972 | 2/2013 | |
| WO | WO 2014/160747 | 10/2014 | |
| WO | WO-2015089322 A1 * | 6/2015 | A61K 38/16 |
| WO | WO-2015157639 A1 * | 10/2015 | |

OTHER PUBLICATIONS

Gonzalez-Navajas et al. Mutation-specific control of BCR-ABL T3151positive leukemia with a recombinant yeast-based therapeutic vaccine in a murine model. Nature Reviews Immunology. Feb. 2012, vol. 12:125-135. Published Online Jan. 6, 2012 (Year: 2012).*

Hartley et al, Pancreatic cancer,treatment options,and GI-4000. Human Vaccines & Immunotherapeutics, Apr. 2015, 11/4:931-937. published online: May 1, 2015 (Year: 2015).*

King et al. Construction and Immunogenicity Testing of Whole Recombinant Yeast-Based T-Cell Vaccines. Sunil Thomas (ed.), Vaccine Design: Methods and Protocols, vol. 2: Vaccines for Veterinary Diseases, Methods in Molecular Biology, 2016 vol. 1404, pp. 529-545 (Year: 2016).*

King et al. A whole recombinant yeast-based therapeutic vaccine elicits HBV X,S and core specific T cells in mice and activates human T cells recognizing epitopes linked to viral clearance. PLoS One, 2014, 9/7:e101904/1-e101904/17, 17 pages, entered STN: Oct. 1, 2014, (abstract only) (Year: 2014).*

Riemann et al, Generation of a prophylactic melanoma vaccine using whole recombinant yeast expressing MART-1. Experimental Dermatology, 2007, 16:814-822 (Year: 2007).*

Singh et al, A phase I study of a yeast-based therapeutic cancer vaccine,GI-6301, targeting brachyury in patients with metastatic carcinoma. (Abstract Only) http://ascopubs.org{doi/abs/10.1200'jco. 2014.32.15_suppl.e14026 (Year: 2014).*

Tamburini et al, IL-6-inducing Whole Yeast-based Immunotherapy Directly Controls IL-12-dependent CD8 T-cell Responses. (J Immunother 2012;35:14-22). (Year: 2012).*

Tsang et al, Yeast vector-encoding multiple MUC1 agonist epitopes (yeast-MUC1) can induce MUC1-specific T-cell immune responses. Cancer Research, (Oct. 1, 2014) vol. 74, No. 19, Suppl. 1. Abstract No. 2561. (Abstract Only) (Year: 2014).*

Vergati et al, Strategies for Cancer Vaccine DevelopmentJournal of Biomedicine and Biotechnology, 2010, Article ID 596432, 13 pages (Year: 2010).*

Wansley et al, Vaccination with a Recombinant *Saccharomyces cerevisiae* Expressing a Tumor Antigen Breaks Immune Tolerance and Elicits Therapeutic Antitumor Responses. Clin Cancer Res 2008;14(13) Jul. 1, 2008 (Year: 2008).*

Axtell et al., "Janus-like effects of type I interferon in autoimmune diseases," Immunological Reviews, 2012, vol. 248, Iss. 1, pp. 23-35.

Baechler et al., "Interferon-inducible gene expression signature in peripheral blood cells of patients with severe lupus," Proceedings of the National Academy of Sciences of the United States of America, 2003, vol. 100, No. 5, pp. 2610-2615.

Bizzini et al. "Use of live *Saccharomyces cerevisiae* cells as a biological response modifier in experimental infections," FEMS Microbiology Immunology, 1990, vol. 64, pp. 155-168.

Brake et al. "Alpha-Factor-directed synthesis and secretion of mature foreign proteins in *Saccharomyces cerevisiae*," Proceedings of the National Academy of Sciences USA, Aug. 1984, vol. 81, pp. 4642-4646.

Crow, "Type I interferon in organ-targeted autoimmune and inflammatory diseases," Arthritis Research & Therapy, 2010, vol. 12, Suppl. 1, S5, 10 pages.

(56) References Cited

OTHER PUBLICATIONS

Dill et al., "Interferon-Induced Gene Expression Is a Stronger Predictor of Treatment Response Than IL28B Genotype in Patients With Hepatitis C," Gastroenterology, 2011, vol. 140, Iss. 3, pp. 1021-1031.
Eto et al., "Immunization with recombinant *Escherichia coli* expressing retinal S-antigen-induced experimental autoimmune uveitis (EAU) in Lewis rats", Cellular Immunology, vol. 147, No. 1 Mar. 1993, pp. 203-214.
Feng et al., "Type I interferon signature is high in lupus and neuromyelitis optica but low in multiple sclerosis," Journal of the Neurological Sciences, 2012, vol. 313, Iss. 1-2, pp. 48-53.
Franzusoff, A. et al. "Yeasts Encoding Tumour Antigens in Cancer Immunotherapy," Expert Opinion on Biological Therapy, Apr. 2005, vol. 5, No. 4, pp. 565-575.
Franzusoff et al. "Biochemical and Genetic Definition of the Cellular Protease Required for HIV-1 gp160 Processing," The Journal of Biological Chemistry, Feb. 1995, vol. 270, No. 7, pp. 3154-3159.
Fujita et al. "Studies in the development of Japanese encephalitis vaccine: expression of virus envelope glycoprotein V3 (E) gene in yeast," Bulletin of the World Health Organization, Feb. 1987, vol. 65, No. 3, pp. 303-308.
Gajewski et al., "Innate immune sensing of cancer: clues from an identified role for type I IFNs," Cancer Immunology, Immunotherapy, 2012, vol. 61, Iss. 8, pp. 1343-1347.
Globeimmune, "Safety and Efficacy of the Therapeutic Vaccine GI-4000 in Combination With Gemcitabine Versus Placebo for the Treatment of Non-metastatic, Post-resection Pancreas Cancer," ClinicalTrials.gov Archive, May 4, 2010, [retrieved on May 19, 2015], 2 pages. Retrieved from: clinicaltrials.gov/archive/NCT00300950/2010_05_04.
González-Navajas et al., "Immunomodulatory functions of type I interferons," (author manuscript). Published in final edited form as: Nature Reviews Immunology, 2012, vol. 12, No. 2, pp. 125-135.
Halwani et al., "T Helper 17 Cells in Airway Diseases: From Laboratory Bench to Bedside," Chest, 2013, vol. 143, No. 2, pp. 494-501.
Häupl et al., "The type 1 interferon signature: facts, fads and fallacies," Annals of the Rheumatic Diseases, 2011, vol. 70, Suppl. 2, p. A24.
Heim, "Interferons and hepatitis C virus," Swiss Medical Weekly, 2012, vol. 142, Iss. 2012/1920, 13 pages.
Hundeshagen et al., "Elevated type I interferon-like activity in a subset of multiple sclerosis patients: molecular basis and clinical relevance," Journal of Neuroinflammation, 2012, vol. 9, 13 pages.
Lu, et al., "Mutation-Selective Tumor Remission with Ras-Targeted, Whole Yeast-Based Immunotherapy," Cancer Research, 2004, vol. 64, pp. 5084-5088.
Klepfer et al. "Characterization of rabies glycoprotein expressed in yeast," Archives of Virology, 1993, vol. 128, pp. 269-286.
Kyogoku et al., "Cell-Specific Type I IFN Signatures in Autoimmunity and Viral Infection: What Makes the Difference?," PLoS One, 2013, vol. 8, Iss. 12, e83776 (16 pages).
Lee et al., "Type I Interferons Maintain Foxp3 Expression and T-Regulatory Cell Functions Under Inflammatory Conditions in Mice," (author manuscript). Published in final edited form as: Gastroenterology, 2012, vol. 143, Iss. 1, pp. 145-154.
McNab et al., "Type I interferons in infectious disease," Nature Review Immunology, 2015, vol. 15, Iss. 2, pp. 87-103.
Moore et al., "Novel yeast-based vaccine against HIV-SF2 gp160 promotes a cytotoxic 43-62 cell response.", FASEB Journal (online), vol. 10. No. 6. 1996, p. A1473, ZP002186594, Joint Meeting of the American Society for Biochemistry and Molecular Biology, the American Society for Investigative Pathology and the American Association of Immunologists; New Orleans, LA, USA; Jun. 2-6, 1996.
Odorizzi et al., "An Interferon Paradox," Science, 2013, vol. 340, Iss.6129, pp. 155-156.
Raglow et al., "IL28B genotype and the expression of ISGs in normal liver," Liver International, 2013, vol. 33, Iss. 7, pp. 991-998.
Schreuder et al. "Yeast expressing hepatitis B virus surface antigen determinants on its surface: implications for a possible oral vaccine," Vaccine, Apr. 1996, vol. 14, No. 5, pp. 383-388.
Sinai et al., "Enhancement of Resistance to Infectious Diseases by Oral Administration of Brewer's Yeast," Infection and Immunity, May 1974, vol. 9, No. 5, pp. 781-787.
Stubbs, et al., "Whole Recombinant Yeast Vaccine Activates Dendritic Cells and Elicits Protective Cell-Mediated Immunity," National Medicine, May 2001, vol. 7, No. 5, pp. 1-5.
Sultanik et al., "Baseline sensitivity of T cells to alpha-IFN correlates with sustained virological response to IFN-based triple therapy in HCV infection," Journal of Viral Hepatitis, 2015, vol. 22, Iss. 6, pp. 524-534.
Teijaro et al., "Persistent LCMV Infection Is Controlled by Blockade of Type I Interferon Signaling," Science, 2013, vol. 340, Iss. 6129, pp. 207-211.
Valenzuela et al. "Antigen engineering in yeast: Synthesis and assembly of hybrid hepatitis B surface antigen-Herpes simplex 1 gD particles", Bio/Technology, Apr. 1985, vol. 3, 323-326.
Wilson et al., "Blockade of Chronic Type I Interferon Signaling to Control Persistent LCMV Infection," Science, 2013, vol. 340, Iss. 6129, pp. 202-207.
Woo et al., "The STING pathway and the T cell-inflamed tumor microenvironment," Trends in Immunology, 2015, vol. 36, Iss. 4, pp. 250-256.
International Search Report and Written Opinion for International (PCT) Patent Application No. PCT/US2015/025316 dated May 15, 2015, 11 pages.
International Preliminary Report on Patentability for International (PCT) Patent Application No. PCT/US2015/025316 dated Oct. 20, 2016, 6 pages.
Habersetzer et al., "GI-5005, a yeast vector vaccine expressing an NS3-core fusion protein for chronic HCV infection," Current Opinion in Molecular Therapeutics, 2009, vol. 11, No. 4, pp. 456-462.
Shiffman et al., "GI-5005 therapeutic vaccine enhances virologic clearance by GEG-IFN/Ribavarin in naive HCV genotype 1 patients with IL28B Genotype T7T," GlobeImmune, 2012 [retrieved on Nov. 21, 2017]. Retrieved from: www.globeimmune.com/wp-content/uploads/2012/04/2012-AASLD-Shiffman-T-T-EOT.pdf.
Extended European Search Report for European Patent Application No. 15776226.1 dated Dec. 4, 2017, 10 pages.
Chaft et al., "Phase II study of the GI-4000 KRAS vaccine after curative therapy in patients with stage I-III lung adenocarcinoma harboring a KRAS G12C, G12D, or G12V mutation," Clinical Lung Cancer, 2014, vol. 15, Iss. 6, pp. 405-410.
Cohn et al. "Whole Recombinant *Saccharomyces cerevisiae* Yeast Expressing Ras Mutations as Treatment for Patients With Solid Tumors Bearing Ras Mutations: Results From a Phase 1 Trial," Journal of Immunotherapy, 2018, vol. 41, Iss. 3, pp. 141-150.
Official Action for European Patent Application No. 15776226.1 dated Sep. 26, 2018, 5 pages.
Shahda et al., "GI-4000 in KRAS mutant cancers," Expert Opinion on Investigational Drugs, 2014, vol. 23, Iss. 2, pp. 273-278.
Official Action (with English translation) for Chinese Patent Application No. 201580030698.4 dated Dec. 27, 2018, 8 pages.
Official Action (English translation) for Chinese Patent Application No. 201580030698.4 dated Oct. 10, 2019, 9 pages.
Official Action for European Patent Application No. 15776226.1 dated Jun. 5, 2019, 5 pages.
Official Action for European Patent Application No. 15776226.1 dated Apr. 29, 2020, 4 pages.
Official Action (English translation) for Chinese Patent Application No. 201580030698.4 dated Jul. 13, 2020, 8 pages.

* cited by examiner

YEAST-BASED IMMUNOTHERAPY AND TYPE I INTERFERON SENSITIVITY

CROSS REFERENCE TO RELATED APPLICATIONS

This application is a national stage application under 35 U.S.C. 371 and claims the benefit of PCT Application No. PCT/US15/25316 having an international filing date of Apr. 10, 2015, which designated the United States, which PCT application claimed the benefit of U.S. Provisional Application No. 61/978,634, filed Apr. 11, 2014, the disclosure of each of which are incorporated herein by reference.

REFERENCE TO SEQUENCE LISTING

This application contains a Sequence Listing submitted as an electronic text file named "3923-48-PUS_Sequence_Listing_ST25.txt", having a size in bytes of 1 byte, and created on Mar. 15, 2018. The information contained in this electronic file is hereby incorporated by reference in its entirety pursuant to 37 CFR § 1.52(e)(5).

FIELD OF THE INVENTION

The present invention generally relates to methods of selecting individuals for treatment with yeast-based immunotherapeutic compositions and methods for enhancing or improving an individual's response to yeast-based immunotherapy, based on the individual's sensitivity to type 1 interferons (T1IFNs).

BACKGROUND OF THE INVENTION

A major goal of immunotherapy is to generate cellular immunity, and in particular, to activate and expand antigen-specific $CD8^+$ effector T cells. There are two well established pathways through which this can occur. The first is via the delivery of "T cell help" provided by $CD4^+$ Th1 cells. A second, more indirect pathway is through the induction of CD4+Th17 cells that, under certain circumstances, can convert into Th1 cells, although their primary role is the production of IL-17 to facilitate the recruitment of macrophages and neutrophils to destroy extracellular bacteria and fungi. Th17 cells also compete for the same space as regulatory T cells (Tregs), and their induction is likely associated with a diminution of Treg activity, thus explaining the correlation between overactive Th17 responses and autoimmunity. These two pathways are antagonistic.

While T1IFNs were originally described as anti-viral mediators, more recent evidence points to an immunomodulatory role for them (Heim, 2012, *Swiss Med Wkly.* 142: w13586; Gonzalez-Navajas et al., 2012, *Nat Rev Immunol.* 12(2):125-35.). For example, T1IFN has been associated with a decrease in Th17 activity (Moschen et al., 2008, *Immunobiology* 213(9-10):779-87), thus providing a plausible explanation for why Tregs are reported to be enhanced by T1IFN (Vandenbark et al., 2009, *J Neuroimmunol.* 215 (1-2):125-8; Lee et al., 2012, *Gastroenterology* 143(1):145-54). T1IFN is thought to suppress the Th17 pathway by targeting IL-1 production (Schindler et al., 1990, *J Immunol.* 144(6):2216-22; Reznikov et al., 1998, *J Interferon Cytokine Res.* 18(10):897-903) and the inflammasome (Guarda et al., 2011, *Immunity* 34(2):213-23), which is necessary for driving the Th17 pathway. T1IFN also induces IL-12 that drives the Th1 pathway (reviewed by Ludigs et al., 2012, *Cell Mol Life Sci.* 69(20):3395-418) and in so doing, reduces IL-23 production associated with Th17 maintenance. T1IFNs are also generally known to suppress cell-mediated immunity and therefore, have been used to treat autoimmune diseases such as multiple sclerosis (MS), in order to target the offending CD4+Th1 and Th17 T cells.

More particularly, some forms of autoimmunity, including MS, rheumatoid arthritis (RA), systemic lupus erythematosus (SLE) and Sjogrens syndrome, have been associated with a "type 1 interferon signal", generically defined as an association between levels of T1IFN activity or response and disease, and more specifically defined by some as unusually high levels of T1IFN activity in the blood or other tissues associated with a reduced (or relatively unchanged) level of responsiveness of type 1 interferon-stimulated genes (ISGs) when exposed to T1IFN (Hooks et al., 1979, *N Engl J Med.* 301(1):5-8; Baechler et al., 2003, *Proc Natl Acad Sci USA.* 100(5):2610-5; reviewed by Crow, 2010, *Arthritis Res Ther.* 12 Suppl 1:S5). The T1IFN signal is being used in the autoimmunity context as a potential diagnostic assay to determine whether patients with MS will respond to T1IFN therapy, a disease in which approximately half of treated individuals appear to respond to the therapy, while other individuals may have worsened autoimmunity as a consequence of treatment. For example, investigators in the MS field have used a PCR approach to measure a T1IFN response gene product, in this case the T1IFN-sensitive MX1 gene (Hundeshagen et al., 2012, *J. Neuroinflamm.* 9:140). In this study, subjects were classified as having either high or low baseline expression of MX1 RNA prior to treatment with the T1IFN, interferon-β (IFN-β). The authors identified a subset of subjects who had low level expression of MX1 RNA at baseline that upregulated the MX1 signal after T1IFN treatment, and a subset of subjects having a higher baseline MX1 RNA level that was unmoved by further T1IFN treatment, showing that individuals can be grouped based on a "T1IFN signature". While these authors were unable to confirm a correlation between an elevated endogenous type I IFN signature (those that did not respond to further T1IFN exposure) and a worse course of disease overall, differences were observed in the relapse rates of the two groups when analyzing the data for each IFN-β drug preparation separately. Axtell et al. (2012, *Immunol. Rev.* 248(1):23-35), reviewed evidence that in MS, high endogenous levels of T1IFN were associated with a Th17 signal defined by higher levels of IL-17 in the blood, proposing that the strong IL-17 signal was a marker for aggressive Th17 driven autoimmunity resistant to the immunosuppressive effects of T1IFN, and that the high levels of endogenous T1IFN activity might reflect an attempt by the host immune system to use endogenous T1IFN as a means to suppress particularly aggressive autoimmunity.

A T1IFN (e.g., pegylated interferon-α, or pegIFN-α) is currently used to treat hepatitis C virus (HCV)-infected individuals (typically administered in combination with an anti-viral drug, such as ribavirin). For HCV, the responders and non-responders to T1IFN therapy have been distinguished by a genotype linked upstream of the interferon IL28B gene locus, where IL28B genotype "C/C" individuals are highly responsive to pegIFN-α/ribavirin therapy, and IL28B genotype "T/T" individuals are unresponsive to pegIFN-α/ribavirin therapy. In a study of HCV-infected individuals, liver biopsy tissue from untreated, HCV-infected subjects was tested for the expression level of four ISGs by PCR prior to the start of treatment (Dill et al, 2011, *Gastroenterology* 140(3):1021-31), to determine whether upregulation of these T1IFN response genes was associated with IL28B genotype and outcome. The authors concluded that while the IL28B genotype and hepatic ISG expression were both associated with response to treatment with pegIFN-α/ribavirin, they were not causally linked, and that the association with ISG was a dominant predictor of outcome. In a publication by Sultanik et al. (2014, *J. Viral Hepat.*), the authors explored IFN-α sensitivity in peripheral blood mononuclear cells (PBMCs) from healthy donors and HCV-infected patients using phosphor-STAT1 levels as a T1IFN biomarker, and showed that baseline sensitivity to IFN-α correlated with positive clinical outcomes, regardless of the IL28B genotype of the patient.

The use of recombinant yeast as a unique immunotherapy (also referred to as yeast-based immunotherapy) has been described (see, e.g., Stubbs et al., 2001, *Nat Med.* 7(5):625-9; Lu et al., 2004, *Cancer Res.* 64(15):5084-8; Haller et al., 2007, Vaccine 25(8):1452-63.; Tamburini et al., 2012, *J Immunother.* 35(1):14-22). Yeast are avidly phagocytosed by professional antigen presenting cells (APCs), such as neutrophils, macrophages and dendritic cells, and multiple antigens can be engineered for expression within a single yeast to elicit multiple, interactive $CD4^+$ T cell-mediated immune responses in vitro and in vivo (Stubbs et al., 2001, supra; Lu et al., 2004, supra; Haller et al., 2007, supra; Bernstein et al., 2008, *Vaccine* 26(4):509-21; Remondo et al., 2009, *Vaccine* 27(7):987-94; Cereda et al., 2011, *Vaccine* 29(31):4992-9.; Riemann et al., 2007, *Exp Dermatol.* 16(10):814-22; Wansley et al., 2008, *Clin Cancer Res.* 14(13):4316-25; Tamburini et al., 2012, supra). These $CD4^+$ T cell subsets include Th17 T cells that compete with and neutralize Tregs, as well as Th1 T cells that help elicit the generation of $CD8^+$ effector T cells. The combined effect of $CD8^+$ T cell generation, with neutralization of Tregs, provides a highly significant immunotherapeutic opportunity that has now been translated into the clinic.

For example, a Phase 2 clinical trial in subjects with chronic HCV infection compared standard of care ("SOC"=pegIFN-α plus ribavirin), to "triple therapy" (SOC combined with the yeast-based immunotherapy product, GI-5005 (a recombinant yeast expressing HCV N53 and Core antigens, GlobeImmune, Inc., Louisville, Colo.)). Triple therapy including GI-5005 significantly improved end of treatment viral clearance and ALT normalization compared to T1IFN-based standard of care (SOC) alone (Jacobson et al., 2010, *European Association for the Study of the Liver* (*EASL*)) and improved sustained virologic response (SVR) by 12% overall, 10% in naïves, and 12% in NR subjects (Pockros et al., 2010, *American Association for the Study of Liver Diseases* (*AASLD*)). Surprisingly, the GI-5005 triple therapy subjects with IL28B T/T genotype had the greatest advantage in sustained virologic response (SVR) as well as IFN-γ ELISpot assay, whereas IL28B T/T subjects receiving SOC alone had notably poorer virologic and IFN-γ ELISpot responses than IL28B C/C and C/T SOC subjects (Vierling et al., 2010, *American Association for the Study of Liver Diseases* (*AASLD*)).

In a Phase 2 clinical trial in pancreas cancer patients using a yeast-based immunotherapy product, GI-4000 (recombinant yeast expressing mutant Ras proteins, GlobeImmune, Inc., Louisville, Colo.), in combination with gemcitabine, a restrospective proteomic analysis using a potential proteomic companion diagnostic test (BDX-001; Biodesix, Inc., Boulder, Colo.) appeared to predict whether a subset of subjects treated with GI-4000 and gemcitabine in this trial would have improved recurrence free survival (RFS) and overall survival (OS) compared to subjects treated with placebo plus gemcitabine. Approximately 50% of the studied subject samples treated with GI-4000 and gemcitabine were classified as BDX-001 positive. In BDX-001 positive subjects treated with GI-4000 and gemcitabine, there was an 11.7 month improvement in median RFS and a 16.6 month improvement in median OS compared with BDX-001 positive subject samples treated with placebo and gemcitabine. BDX-001 did not predict response for placebo/gemcitabine treated subjects (Richards et al., 2012, *European Society for Medical Oncology* (*ESMO*); Richards et al., 2014, *American Association for Cancer Research* (*AACR*)).

Accordingly, in these clinical studies, there appears to be a subset or subsets of patients that benefit more from the immunotherapy than other patients. However, the connection between the responders in these very different disease types, if any, is not clear based on the available data from the studies, nor has it been identified whether there are other biomarkers that can be generally used to select subjects most likely to respond to yeast-based immunotherapy. Therefore, there remains a need to understand how to identify the subjects that are most responsive to yeast-based immunotherapy generally, as well as the underlying mechanism for this phenotype, and to develop a method to select and then treat subjects who are most likely to have a beneficial response to yeast-based immunotherapy in a variety of diseases. Indeed, it would be very useful to be able to identify whether a person would respond or not to avoid subjecting them to a therapy for which there would be no clear benefit.

SUMMARY OF THE INVENTION

One embodiment of the invention relates to a method to treat a subject with yeast-based immunotherapy, comprising administering a yeast-based immunotherapy composition to a subject who has been preselected as being sensitive to type 1 interferon (T1IFN). In one aspect, T1IFN-naïve peripheral blood mononuclear cells (PBMCs) from the subject up- or down-regulate a T1IFN-regulated biomarker as a result of contact with T1IFN. In one aspect, PBMCs from the subject that were previously responsive to T1IFN exposure are refractory to further exposure to T1IFN.

Another embodiment of the invention relates to a method to treat a subject with yeast-based immunotherapy. The method includes the steps of: (a) preselecting a subject who is sensitive to T1IFN; and (b) administering yeast-based immunotherapy to the subject. In one aspect, the step (a) of preselecting comprises preselecting a subject whose level of one or more T1IFN-regulated biomarkers changes at least three-fold as a result of contacting a biological sample from the subject ex vivo or in vitro with T1IFN. In one aspect, the step (a) of preselecting comprises preselecting a subject whose level of one or more T1IFN-regulated biomarkers changes at least five-fold as a result of contacting a biological sample from the subject ex vivo or in vitro with T1IFN.

In one aspect of any of these embodiments or methods of the invention, the step (a) of preselecting comprises the steps of: (i) measuring a baseline level of one or more T1IFN-regulated biomarkers ex vivo or in vitro in a biological sample isolated from the subject; (ii) contacting the biological sample with T1IFN; (iii) measuring the level of the one or more T1IFN-regulated biomarkers after step (ii) of contacting; and (iv) preselecting T1IFN-sensitive subjects for treatment with yeast-based immunotherapy whose level of the one or more T1IFN-regulated biomarker was up- or down-regulated as a result of contacting the biological sample with T1IFN. In one aspect, step (i) and/or (iii) of measuring comprises using an assay that can include, but is not limited to: enzyme-linked immunosorbant assay (ELISA), real-time polymerase chain reaction (PCR), flow cytometry, multiplex bead-based immunoassay, or quantitative selected reaction monitoring (SRM)-based mass spectrometry. In one aspect, subjects are preselected whose level of the one or more T1IFN-regulated biomarker was up- or down-regulated at least three-fold from the baseline level as a result of contacting the biological sample with T1IFN. In one aspect, subjects are preselected whose level of the one or more T1IFN-regulated biomarker was up- or down-regulated at least five-fold from the baseline level as a result of contacting the biological sample with T1IFN.

In one aspect of the methods described herein, the step (a) of preselecting comprises the steps of: (i) measuring a baseline level of one or more T1IFN-regulated biomarkers ex vivo or in vitro in a biological sample isolated from the subject; (ii) contacting the biological sample with T1IFN; (iii) measuring the level of the one or more T1IFN-regulated biomarkers after step (ii) of contacting; (iv) contacting the biological sample with T1IFN after step (iii); (v) measuring the level of the one or more T1IFN-regulated biomarkers after step (iv) of contacting; and (vi) preselecting T1IFN-sensitive subjects for treatment with yeast-based immunotherapy whose level of the one or more T1IFN-regulated biomarker was up- or down-regulated as a result of contacting the biological sample with T1IFN in step (ii), and whose level of the one or more T1IFN-regulated biomarker was not substantially up- or down-regulated as a result of contacting the biological sample with T1IFN in step (iv). In one aspect, the step (i) and/or (iii) and/or (v) of measuring comprises using an assay selected from, but not limited to: enzyme-linked immunosorbant assay (ELISA), real-time polymerase chain reaction (PCR), flow cytometry, multiplex bead-based immunoassay, or quantitative selected reaction monitoring (SRM)-based mass spectrometry.

Yet another embodiment of the invention relates to a method to treat cancer or a disease caused by a pathogen with yeast-based immunotherapy. The method includes the step of administering a yeast-based immunotherapy composition to a subject who has cancer or a disease caused by a pathogen, whose level of one or more T1IFN-regulated biomarkers changes at least three-fold as a result of contacting a T1IFN-naïve biological sample from the subject ex vivo or in vitro with T1IFN.

In any of the above-described embodiments and methods of the invention, in one aspect, the biological sample has not been exposed to exogenous T1IFN prior to preselecting the subject. In another aspect, the subject has not received an exogenous source of T1IFN prior to step (a). In another aspect, the biological sample is peripheral blood mononuclear cells (PBMCs). In another aspect, the biological sample is a tissue biopsy from the subject.

In any of the above-described embodiments of the invention, in one aspect, cells in the biological sample upregulate one or more type 1 interferon-stimulated genes (ISGs) as a result of contact with T1IFN ex vivo or in vitro. In one aspect, a T1IFN-regulated biomarker in the biological sample has increased phosphorylation as a result of contact with T1IFN ex vivo or in vitro. In one aspect, cells in the biological sample produce a higher level of T1IFN-regulated protein as a result of contact with T1IFN ex vivo or in vitro.

In any of the above-described embodiments and methods of the invention, in one aspect, the T1IFN is interferon-α. In one aspect, the T1IFN is interferon-β.

In any of the above-described embodiments and methods of the invention, in one aspect, the subject has cancer. In one aspect, the subject has an infectious disease.

In any of the above-described embodiments and methods of the invention, in one aspect, the yeast-based immunotherapy includes administration of whole yeast that have recombinantly expressed one or more antigens.

Yet another embodiment of the invention relates to a method of preselecting a subject for treatment with yeast-based immunotherapy. The method includes the steps of: (a) measuring a baseline level of one or more T1IFN-regulated biomarkers ex vivo or in vitro in a biological sample isolated from a subject who is a candidate for yeast-based immunotherapy; (b) contacting the biological sample with T1IFN ex vivo or in vitro; (c) measuring the level of the one or more T1IFN-regulated biomarkers after step (b) of contacting; and (d) preselecting T1IFN-sensitive subjects for treatment with yeast-based immunotherapy whose level of the one or more T1IFN-regulated biomarker was up- or down-regulated as a result of contacting the biological sample with T1IFN. In one aspect, subjects are preselected whose level of the T1IFN-regulated biomarker measured after contact with the T1IFN as compared to the level of the T1IFN-regulated biomarker measured before contact with the T1IFN is detectable over background. In one aspect, subjects are preselected whose level of the T1IFN-regulated biomarker measured after contact with the T1IFN as compared to the level of the T1IFN-regulated biomarker measured before contact with the T1IFN is statistically significantly different. In one aspect, subjects are preselected whose ratio between the level of the T1IFN-regulated biomarker measured after contact with the T1IFN and the level of the T1IFN-regulated biomarker measured before contact with the T1IFN is at least three. In one aspect, subjects are preselected whose ratio between the level of the T1IFN-regulated biomarker measured after contact with the T1IFN and the level of the T1IFN-regulated biomarker measured before contact with the T1IFN is at least five. In one aspect, step (a) and/or (c) of measuring comprises using an assay selected from, but not limited to: enzyme-linked immunosorbant assay (ELISA), real-time polymerase chain reaction (PCR), flow cytometry, multiplex bead-based immunoassay, or quantitative selected reaction monitoring (SRM)-based mass spectrometry. In one aspect, the biological sample is peripheral blood mononuclear cells (PBMCs) isolated from the subject. In one aspect, the biological sample is a tissue biopsy from the subject.

BRIEF DESCRIPTION OF THE DRAWINGS OF THE INVENTION

DETAILED DESCRIPTION OF THE INVENTION

Figure 1:
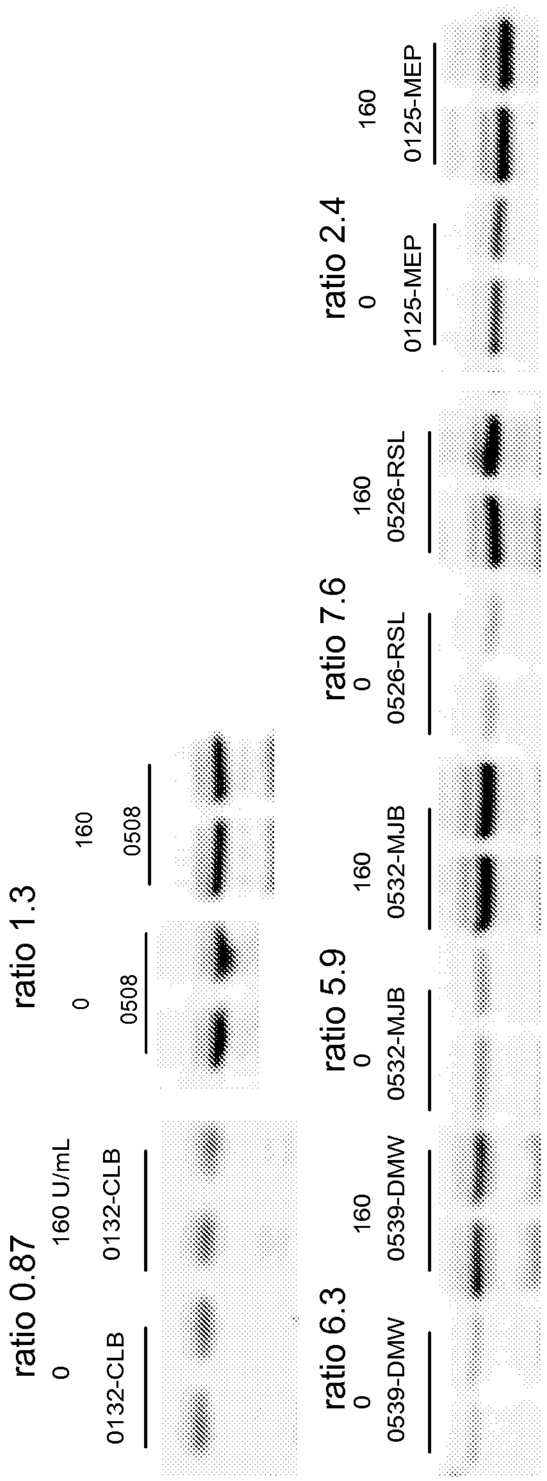
FIG. 1 is a digital image of a Western blot showing, for peripheral blood mononuclear cell (PBMC) samples from six different patients who received a yeast-based immunotherapy, the ratio of quantified M×A protein before T1IFN addition (lane denoted "0") versus quantification of M×A protein after T1IFN addition (lane denoted "160 U/mL").

This invention generally relates to methods for treating individuals with yeast-based immunotherapy who are pre-selected to be most likely to respond to such therapy, and also to methods for selecting these individuals, as well as methods for enhancing or improving a selected individual's response, or the ability to respond, to yeast-based immunotherapy. The invention includes the use of yeast-based immunotherapeutic compositions (also referred to as "yeast-based immunotherapy") comprising a yeast vehicle and one or more antigen(s) that have been designed to elicit a prophylactic and/or therapeutic immune response against a target in an individual, and the use of such compositions to prevent and/or treat a variety of diseases, conditions, and related symptoms thereof. Individuals selected as most likely to respond to yeast-based immunotherapy (i.e., produce an immune response to the immunotherapy that is beneficial in ameliorating or treating a disease or condition) are, according to the present invention, selected on the basis of the "type 1 interferon (T1IFN) signature" of the individual. More specifically the present invention relates to the administration of yeast-based immunotherapy to individuals who are pre-selected on the basis of their sensitivity to type 1 interferons, i.e., are selected as "interferon-sensitive" or "interferon-responsive" or individuals having a "T1IFN sensitive signature" (described in detail below). As discussed in more detail below, such individuals may also be sensitive to T1IFN such that repeated exposure to T1IFN after an initial baseline exposure can result in desensitization of the individual's cells to T1IFN (i.e., further repeated exposure to T1IFN does not induce a further response to T1IFN for at least a period of time).

Various aspects of the immune response of subjects treated with yeast-based immunotherapy in preclinical and clinical studies have previously linked both genotypic (IL28B) and phenotypic ($CD4^+$ Th1/Th17 T cells, $CD8^+$ T cells, Treg, and cytokine) identifiers that are associated with results achieved in the clinic. However, the relationship between an individual's sensitivity or insensitivity to T1 IFNs and the effects of yeast-based immunotherapy on the individual remained unclear prior to the present invention. The range of immune responses that can be initiated by yeast-based immunotherapy is complex, and may include interferon-independent capabilities; however, it is now clear that the T1IFNs play an important role in the ability of an individual to respond to yeast-based immunotherapy, which was not known or understood prior to the present invention. Indeed, yeast-based immunotherapy has been used in preclinical or clinical studies in both the presence and absence of exogenous T1IFN, and in diseases where the causative agent can actively induce intrinsic T1IFN activity (e.g., viral disease, such as HCV) and diseases where the relationship between T1IFN and immune responses are still unclear (e.g., cancer). Further complicating the analysis is the knowledge that yeast themselves induce T1IFN production (Biondo et al, 2011; Bougeois et al, 2011; Kasperkovitz et al, 2011; Majer et al, 2012; Smeekens et al, 2013). Therefore, it could be argued, for example, that the responders to yeast-based immunotherapy are those who are most sensitive to T1IFN. T1IFN signaling has been described to directly act on T cells since it can induce the production of IFN-γ, thus favoring induction and maintenance of Th1 T cells (Brinkman et al, 1993; Krug et al, 2003). In this case, the Th17 pathway induced by yeast-based immunotherapy might actually be an impediment to responsiveness, and treating with T1IFN might mitigate to some extent this interference. Thus, sensitivity to T1IFN would enhance the Th1 pathway, driving the $CD8^+$ T cell-mediated immune response, and leading to a better outcome for patients treated with yeast-based immunotherapy. Alternatively, it could be argued that the responders to yeast-based immunotherapy are those who are most resistant to or can develop resistance to T1IFN (T1IFN-insensitive individuals). This would drive the Th17 pathway and degrade regulatory T cells, thus allowing a more potent effector immune response to occur. Prior to the present invention, the correct answer was not known.

The concept of a T1IFN signature that would identify an individual as either sensitive to T1IFN or insensitive (or less sensitive) to T1IFN has been applied for the first time by the present inventors to yeast-based immunotherapy, to discover among at least two populations of people, denoted here as T1IFN-sensitive (which may also be referred to as T1IFN-responsive) and T1IFN-insensitive (which may also be referred to as T1IFN-resistant, T1IFN-nonresponsive or T1IFN-less responsive), which subset is most responsive to the yeast-based immunotherapy (which induces T1IFN, Th1 T cells, and Th17 T cells). The present inventors, without being bound by theory, believe that in the presence of yeast, which induces competing Th1 and Th17 pathways, the T1IFN induced by yeast serves to modulate the Th17 pathway, and thus ensure a more balanced parallel generation of some Th1-driven $CD8^+$ T cell responses. In addition, the modulated Th17 T cell responses driven by the yeast further downregulates Treg activity or survival, enhancing the ability of the Th1 and $CD8^+$ effector responses to occur. Evidence provided by the data presented herein indicate that clinical outcomes observed upon administration of yeast-based immunotherapy associate with individuals who are more sensitive to T1IFN (T1IFN-sensitive individuals), i.e. clinical responders have immune systems that are skewed towards a Th1 response in the presence of yeast-based immunotherapy, while reduced or absent clinical response is associated with individuals who are less sensitive to T1IFN (T1IFN-insensitive individuals), i.e., individuals whose immune systems are biased toward a Th17 immune response in the presence of yeast-based immunotherapy.

More specifically, and without being bound by theory, the inventors propose the following mechanism of action supporting the discovery described herein. Yeast-based immunotherapy first engages Toll-Like Receptors (TLRs) such as TLR 2 and TLR 4 on the surface of antigen presenting cells (APCs). This leads to the induction of cytokine production by the APC that include interleukin-6 (IL-6), IL-23 and IL-1β. IL-1β, IL-6 and IL-23 all drive the Th17 pathway. Thus, Th17 T cells are likely poised to be activated by yeast-based immunotherapy. However, because IL-23 and IL-12 share the same heavy chain, APCs such as dendritic cells (DCs) are also positioned to make IL-12, which occurs most effectively when yeast-based immunotherapy compositions are internalized, during which time the yeast DNA induces TLR 7 and 9, leading to the production of T1IFNs. T1IFN is either necessary or critically important for the induction of IL-12, in part because T1IFN also inhibits the production of active IL-113. This impairs IL-23 generation and thus Th17 expansion. The combined effect of yeast-induced T1IFN and IL-12, to the detriment of IL-1β and IL-23, drives the Th1 pathway. At this juncture, yeast-based immunotherapy has essentially induced concomitant development of both Th17 and Th1 T cells.

The balance between Th1 and Th17 pathways is precarious, however, and yeast-induced T1IFN/IL-12-mediated expansion of Th1 T cells diminishes Th17 T cell induction, as does IFN-γ produced by Th1 T cells and $CD8^+$ T cells. At this point, the balance of power is thus shifting from a Th17 pathway to a Th1 pathway. However, T1IFN-dependent Th17 T cell diminution also leads to lack of control of Treg generation, since Th17 T cells otherwise limit Treg generation. The Tregs are then free to suppress the Th1 response, leading to the cessation of $CD8^+$ T cell effector generation.

Consequently, if an individual is T1IFN-sensitive according to the present invention, the individual can use T1IFN to propel the Th1 pathway and the subsequent generation of $CD8^+$ effector cells. However, if the individual is less sensitive or resistant to T1IFN, then the Th17 pathway can be unencumbered by the suppressive effects of T1IFN. Thus, the individual drives the Th17 pathway to the detriment of Th1 and $CD8^+$ T cells, as well as Tregs. In diseases or conditions where positive outcomes are associated with Th1 T cell and $CD8^+$ T cell responses, such as cancer, viral infection and infection by various other extracellular or intracellular pathogens, T1IFN-sensitivity is important.

It is proposed herein for the first time that a previously unknown factor for identifying individuals who are most likely to respond to yeast-based immunotherapy in a clinically meaningful way, as well as individuals who are least likely to respond to yeast-based immunotherapy in a clinically meaningful way, is T1IFN-sensitivity (most likely to respond), or conversely, T1IFN-insensitivity, (least likely to respond). An assay was developed to test T1IFN sensitivity and analyze a test cohort of subjects who were treated with yeast-based immunotherapy (see Examples). The data show that for both overall survival (OS) and recurrence free survival (RFS), those individuals who are T1IFN-sensitive, as further defined herein, are more likely to be responders to yeast-based immunotherapy for pancreas cancer. Even with this small subset there is statistical significance. Importantly, the association with T1IFN-sensitivity that is the subject of the present invention was specifically associated with yeast-based immunotherapy outcomes, and not with outcomes based on the use of other therapies, e.g., chemotherapy alone, in the context of cancer.

Accordingly, the present invention describes the discovery that yeast-based immunotherapy that induces both T1IFN and protective T cell mediated immunity will be most beneficial in subjects who are genetically predisposed to be sensitive to T1IFN, or who can develop sensitivity to T1IFN. The invention relates to the ability to preferentially select for treatment those subjects who are defined as, or who can develop over time, this appropriate response to T1IFN. The ability to identify probable responders prior to or early in the treatment approach will yield better predictions of response to treatment with yeast-based immunotherapy, providing a significant benefit to an individual being treated.

Methods for Identifying or Preselecting for Yeast-Based Immunotherapy Treatment Accordingly, the present invention centers on the use of yeast-based immunotherapy for the treatment or prevention of diseases, including infectious diseases (or diseases caused by a pathogen) and cancer, by disclosing methods to preselect individuals who are likely to have the best outcomes, specifically, by preselecting subjects who are sensitive to T1IFN. Accordingly, one embodiment of the present invention relates to a method to treat a subject with yeast-based immunotherapy, which includes administering a yeast-based immunotherapy composition to a subject who has been preselected as being sensitive to T1IFN. The step of "preselecting" the subject is performed by conducting a preselection method (i.e., assay, analysis, test) on a biological sample from the subject (which may be performed in vivo or ex vivo or in vitro, but is most typically performed ex vivo or in vitro) to detect whether the subject, and in particular, the immune system of the subject, is sensitive or not sensitive (or less sensitive) to T1IFN. The reference to performing the assay in vitro or ex vivo refers to performing the assay in the laboratory on a biological sample (e.g., cells, tissue, fluid, etc.) that has been removed from the body. Some of skill in the art may consider this to be "ex vivo" and some of skill in the art may consider this to be "in vitro", but in this context, for clarity, the terms may be used interchangeably.

One embodiment of the invention includes a method to preselect a subject for treatment with yeast-based immunotherapy. This method includes the steps of: (a) measuring a baseline level of one or more T1IFN-regulated biomarkers ex vivo or in vitro in a biological sample (e.g., cells) isolated from the subject; (b) contacting the biological sample with T1IFN ex vivo or in vitro; (c) measuring the level of the one or more T1IFN-regulated biomarkers after step (b) of contacting; and (d) preselecting T1IFN-sensitive subjects for treatment with yeast-based immunotherapy whose level of the one or more T1IFN-regulated biomarkers was up- or down-regulated as a result of contacting the biological sample with T1IFN. In one aspect of the invention, a ratio of the level of biomarker measured in step (c) to the level of biomarker measured in step (a) is calculated, which is then used to preselect the subject as a candidate, or to reject the subject as a candidate, for treatment with yeast-based immunotherapy. In some embodiments, a predetermined cutoff or standard (described below) is used to preselect the subject (or to reject or otherwise deselect the subject).

In one aspect of the invention, the above-described method additionally includes, after step (c), the following steps: (d) contacting the biological sample with T1IFN ex vivo or in vitro after step (c); (e) measuring the level of the one or more T1IFN-regulated biomarkers after step (d) of contacting; and (f) preselecting T1IFN-sensitive subjects for treatment with yeast-based immunotherapy whose level of the one or more T1IFN-regulated biomarker was up- or downregulated as a result of contacting the biological sample with T1IFN in step (b), and whose level of the one or more T1IFN-regulated biomarkers was not substantially up- or downregulated as a result of contacting the biological sample with T1IFN in step (d). In this method, subjects are being selected for not only showing T1IFN-sensitivity in the first portion of the assay (steps (a)-(c)), but also for showing that after a first exposure to T1IFN, the cells become desensitized to further or repeated exposure to T1IFN, which may be useful in screening for those subjects who are most sensitive to T1IFN. This aspect of the invention is described in detail below.

Another embodiment of the invention relates to a method to analyze an individual's response to T1IFN in order to determine the responsiveness of the subject to yeast-based immunotherapy. In this embodiment of the invention, the level of a T1IFN-responsive biomarker is measured in a biological sample from the subject before and after the biological sample is exposed to T1IFN, and the ability of the biological sample (or component in the biological sample, such as a cell) to respond to exposure to T1IFN as compared to before exposure to T1IFN is determined.

In one aspect of the methods of preselecting or analyzing of the invention, the subject's biological sample (e.g., cells) have not been exposed to exogenous type I interferon prior to preselecting the subject. In this aspect, the goal is to maximize the ability to compare a relatively intrinsic level of T1IFN-sensitivity to a post-T1IFN exposure sensitivity, to determine the state of the baseline immune response in the subject. Accordingly, in another aspect of these methods of the invention, it may be preferred that the subject has not received an exogenous source of type I interferon prior to step (a), although such subjects may also be tested and preselected in accordance with the invention.

In one optional aspect of the methods of preselecting or analyzing of the invention, an additional test is described. In this additional test, a sample of the subject cells containing T cells is tested to detect whether the T cells proliferate, or do not proliferate (or exhibit low proliferation) in response to contact with APCs that have been exposed to or incubated with a yeast-based immunotherapy composition. It is expected that subjects who are sensitive to T1IFN will also have T cells that proliferate in this secondary assay, and proliferate to a greater degree than T cells from subjects who are less sensitive, or insensitive to T1IFN. Methods for measuring T cell proliferation are well known in the art. For example, T cell proliferation is typically measured in vitro, by obtaining T cells from the subject and exposing them to antigen presenting cells that have been contacted with the yeast-based immunotherapeutic composition, and measuring proliferation of the T cells, such as by using a radioisotope or colorimetric detection method.

According to the present invention, the term "interferon" generally refers to a cytokine that is typically produced by cells of the immune system and by a wide variety of other cells in response to the presence of double-stranded RNA or other T1IFN-inducing stimuli. A "type 1 interferon" or "T1IFN" can include any member of a subgroup of interferon proteins that are known in the art and that can be identified, for example, by their ability to bind to a specific cell surface receptor complex known as the interferon-α receptor (IFNAR), which consists of IFNAR1 and IFNAR2 chains (De Weerd et al., 2007, *J Biol Chem* 282 (28): 20053-20057). The IFNAR associates with kinases TYK2 and JAK1. Once activated, the IFNAR complex phosphorylates signal transducers and activators of transcription (STAT) family members, STAT1 and STAT2, which heterotrimerize with interferon regulatory factor 9 (IRF9) to form the interferon-stimulated gene factor 3 (ISGF3) complex (Janus kinase (JAK)/STAT pathway). ISGF3 translocates to the nucleus and binds the interferon-stimulated response element (ISRE), a DNA motif that can be found in the regulatory region of many interferon-stimulated genes (ISGs) (reviewed in Hundeshagen, 2012, supra). There are also several positive and negative feedback loops in the T1IFN-related pathways.

T1IFNs that are found in mammalian systems include, but may not be limited to, IFN-α, IFN-β, IFN-κ, IFN-δ, IFN-ε, IFN-τ, IFN-ω, and IFN-ζ (also known as limitin). T1IFNs found in humans include IFN-α, IFN-β, IFN-κ (also known as IFNK), and IFN-ω. IFN-α proteins, of which there are various subtypes (including IFN-α-2a and IFN-α-2b), IFN-β proteins, of which there are various subtypes (including IFN-β-1a and IFN-β-1b), are produced by many cell types including lymphocytes, macrophages, plasmacytoid dendritic cells, fibroblasts, endothelial cells, and others, and are typically involved in innate immune responses. IFN-α is also produced commercially for administration to humans to treat various diseases, including HCV, certain other viral infections and some cancers, and is most often provided in commercially in a pegylated form (e.g., pegIFN-α). IFN-β is also produced commercially to treat various diseases, including MS.

According to the present invention, the term "T1IFN signature" or "IFN signature" as used commonly in the art, refers to the differential expression of interferon-inducible (and in the case of T1IFN, T1IFN-inducible) genes, which has been used in the art to distinguish, for example, patients with a disease, such as an autoimmune disease, from individuals who do not have the disease (normal or healthy). An interferon signature may be established for a given cell type and/or a given tissue type, and/or a given disease state (e.g., autoimmune disease or viral infection), and the number and identity of T1IFN-inducible genes that are expressed by a cell, tissue or individual in response to exposure to a T1IFN may differ based on these parameters. For the purposes of the present invention, it is not necessary to know the exact T1IFN signature for the given cell type, tissue type, other sample type, or individual to be tested, or to test for the expression of all genes or other biomarkers that are responsive to T1IFN in a given cell, tissue, other sample type or individual. The invention relates to differences in the ability of an individual to modulate the level of one or more T1IFN-responsive biomarkers in response to T1IFN in a manner that indicates responsiveness to T1IFN, in order to determine whether a subject is sensitive or insensitive to T1IFN.

As mentioned above, the evaluation of "T1IFN signatures", along with other scientific research, has resulted in the identification of a variety of biomarkers, which include genes, mRNA, proteins and even phosphorylation patterns that are responsive to T1IFN by inducing endogenous T1IFN pathways or by being regulated (e.g., by modulation of expression or production) by exposure to T1IFN. Such biomarkers are generally referred to herein as "T1IFN biomarkers" and can also be referred to as, or include, type 1 "T1IFN-regulated biomarkers", "T1IFN-stimulated biomarkers", "interferon-stimulated genes" (or "ISGs") or genes that have an "interferon-stimulated response element" (or ISRE), products of ISGs (e.g., the protein products encoded by ISGs), or "interferon-responsive" elements or genes or proteins (or any derivation of these terms). T1IFN biomarkers useful in the present invention include any T1IFN biomarker known in the art, such as those described in: Blasius et al., 2010, *Immunity* 32:305-315; Bonjardim et al., 2009, *Immunol Lett* 122:1-11; Boo et al., 2010, *Yonsei Med J* 51:9-17; Borden et al., 2007, *Nat Rev Drug Discov* 6:975-990; Fensterl et al., 2009, *Biofactors* 35:14-20; Hall et al., 2010, *Nat Rev Rheumatol* 6:40-49; Haller et al., 2007, *Cytokine Growth Factor Rev* 18:425-433; Koyama et al., 2008, *Cytokine* 43:336-341; Sadler et al., 2008, *Nat Rev Immunol* 8:559-568; Takaoka et al., 2006, *Cell Microbiol* 8:907-922; Zhang et al., 2007, *Immunol Rev* 220:225-236; Hundeshagen et al., 2012, supra; Kyogoku et al., 2013, *PLoS ONE* 8(12): e83776; Schneider et al., 2014, *Annual Review of Immunology*, 32: 513-545; and Waddell et al., 2010, *PLos One* 5(3) e9753.

T1IFN biomarkers useful in the invention include, but are not limited to, the genes known as: MX1 (encoding protein myxovirus (influenza virus) resistance 1, also known as M×A), STAT1 (encoding signal transducers and activators of transcription family 1), IFNAR1 (encoding interferon alpha/beta receptor alpha chain), IFNAR2 (encoding interferon alpha/beta receptor beta chain), IFI44L (encoding interferon-induced protein 44-like), RSAD2 (encoding radical S-adenosyl methionine domain containing 2), ISG15 (encoding interferon-stimulated gene 15), IFI27 (encoding interferon-inducible protein 27), LAMP3 (encoding lysosomal-associated membrane protein 3), OAS1/2 and OA53 (encoding 2'-5'-oligoadenylate synthetase 1, 2 or 3), CXCL10 (encoding C—X—C motif chemokine 10), SEB2 (encoding the beta subunit of the Sec61p ER translocation complex), CEACAM1 (encoding Carcinoembryonic antigen-related cell adhesion molecule 1), SOC3 (encoding Suppressor of cytokine signaling 3), TRAF2 (encoding TNF receptor-associated factor 2), MAP2K6 (encoding mitogen-activated protein kinase kinase 6), THBS1 (encoding thrombospondin 1), HBEGF (encoding Heparin-binding EGF-like growth factor), ID1 (encoding immediate dose interferon), NR4A1 (encoding nuclear receptor subfamily 4, group A, member 1), DEFB1 (encoding defensin, beta 1), FOSL1 (encoding FOS-like antigen 1), EREG (encoding epiregulin), FOSL2 (encoding FOS-like antigen 2), ABRN (encoding active breakpoint cluster region (BCR)-related protein), CCL7 (encoding chemokine (C—C motif) ligand 7), CD9 (encoding complementary determining protein 9), ETNK1 (encoding ethanolamine kinase 1), C5AR1 (encoding complement component 5a receptor 1), SUV420h1 (encoding suppressor of variegation 4-20 homolog 1), MYB (encoding v-myb avian myeloblastosis viral oncogene homolog), SOS1 (encoding son of sevenless homolog 1), CD4 (encoding complementary determining protein 4), CD38 (encoding complementary determining protein 38), CD69 (encoding complementary determining protein 69), VEGFA (encoding vascular endothelial growth factor A), LGALS3BP (encoding lectin, galactoside-binding, soluble, 3 binding protein), GZMB (encoding granzyme B (granzyme 2, cytotoxic T-lymphocyte-associated serine esterase 1)), SPHK1 (encoding sphingosine kinase 1), PRF1 (encoding perforin 1), PGAP1 (encoding post-GPI attachment to proteins 1), EGR3 (encoding early growth response 3), TNIK (encoding TRAF2 and NCK interacting kinase), GZMA (encoding granzyme A (granzyme 1, cytotoxic T-lymphocyte-associated serine esterase 3)), CXXC5 (encoding COX finger protein 5), S100A12 (encoding S100 calcium-binding protein A12), BLNK (encoding B cell linker), GOS2 (encoding G0/G1 switch 2), PDLIM7 (encoding PDZ and LIM domain 7), SLC2A3 (encoding solute carrier family 2 (facilitated glucose transporter), member 3), MXD1 (encoding MAX dimerization protein 1), FAIM2 (encoding Fas apoptotic inhibitory molecule 2), E1F2AK2 (encoding eukaryotic translation initiation factor 2 alpha kinase 3), PRKRA (encoding protein kinase, interferon-inducible double stranded RNA dependent activator), PALM2 (encoding paralemmin 2), EIF2B1 (encoding eukaryotic translation initiation factor 2 subunit), FAS (encoding Fas cell surface death receptor), FASLG (encoding Fas ligand), FAF1 (encoding Fas (TNFRSF6) associated factor 1), GADD45B (encoding growth arrest and DNA-damage-inducible, beta), and/or IL15RA (encoding interleukin-15 receptor alpha), and may include protein products of those biomarkers that are genes or other biomarkers (e.g., myxovirus (influenza virus) resistance 1 (MX1 or M×A), protein kinase R (PKR), 2'-5'-oligoadenylate synthetase (OAS), (interferon-induced transmembrane protein (IFITM), apolipoprotein B mRNA-editing enzyme 1 (APOBEC1), tripartite motif-containing proteins (TRIM)), as well as phosphorylation levels of such protein products (e.g., phosphorylation of STAT1).

The present invention includes the measurement of at least one T1IFN biomarker. In one embodiment, 1, 2, 3, 4, 5, 6, 7, 8, 9, 10, 11, 12, 13, 14, 15, 16, 17, 18, 19, 20, 21, 22, 23, 24, 25, or more T1IFN biomarkers are used in the same assay (or sequentially performed assays on the same biological sample or aliquots of such sample) in order to measure T1IFN-sensitivity of an individual.

According to the present invention, "T1IFN-sensitive", which may also be referred to as "T1IFN-responsive", is most generally defined herein as the ability of an individual to exhibit a detectable and/or biologically meaningful physiological response upon exposure to T1IFN, as measured by a detectable change in one or more biomarkers that are regulated, activated, induced, or modulated by a T1IFN as compared to prior to exposure to T1IFN, whereby the change can be detected in vivo or ex vivo or in vitro. A "biologically meaningful" physiological response, in the context of the present invention, is a response that is sufficient to reasonably classify a subject as more likely to respond to yeast-based immunotherapy, at least to a degree acceptable to recommend or prescribe this treatment for the subject. A biologically meaningful response may, in one embodiment, be statistically significant, and/or a level that has been designated by validation of a particular assay. Validation generally refers to performing all of the procedures that demonstrate that a particular method used for quantitative measurement of a parameter in a biological sample is reliable and reproducible for the intended use. A "detectable" change will be described in more detail below, but most generally means that the change can be detected using an art-accepted or validated technique for measuring the chosen T1IFN biomarker(s) and in preferred embodiments, a "detectable" change useful for identifying T1IFN-sensitive individuals is a level of change that is significant or sufficient to conclude that the subject is reasonably likely to respond to yeast-based immunotherapy, or that the subject is more likely to respond to yeast-based immunotherapy as compared individuals having a lesser level of change. According to the present invention, a T1IFN-sensitive individual may also, in some embodiments, be characterized by one or more of the following attributes: (1) exhibiting Th1-dominant immune responses, as compared to Th17 immune responses; (2) having low or relatively low serum IL-17 levels; (3) having low or relatively low serum T1IFN levels; (4) having $CD4^+$ T cells that expand in response to contact with APCs that have phagocytosed a yeast-based immunotherapy composition; (5) having immune cells responsive to PD-1 blockade (e.g., respond to inhibition of PD-1, such as by anti-PD1 antibodies); and/or (6) having enhanced levels of indoleamine-pyrrole 2,3-dioxygenase (IDO) produced by the immune system as a consequence and downstream effect of T1IFN production. In one embodiment, T1IFN-sensitive individuals can also be identified by their response to repeated in vitro/ex vivo exposure to T1IFN (i.e., at least two sequential exposures), wherein T1IFN-sensitive individuals are more likely to become desensitized rather than sensitized to T1IFN upon the subsequence exposures to T1IFN.

According to the present invention, "T1IFN-insensitive", which may also be referred to as "T1IFN-resistant", "T1IFN-less responsive" or "T1IFN-nonresponsive", is most generally defined as the inability or low ability of an individual (or reduced ability as compared to a T1IFN-sensitive individual), to exhibit a detectable and/or biologically meaningful physiological response to exposure to T1IFN, as measured by a detectable change in one or more biomarkers that are regulated, activated, induced, or modulated by a T1IFN (e.g., as compared to prior to exposure to T1IFN), whereby the change can be detected in vivo or ex vivo or in vitro. According to the present invention, a T1IFN-insensitive individual may also, in some embodiments, be characterized by one or more of the following attributes: (1) exhibiting Th17-dominant immune responses, as compared to Th1 immune responses; (2) having high or relatively high serum IL-17 levels; (3) having high or relatively high serum T1IFN levels; (4) having $CD4^+$ T cells that do not expand or have little to no proliferation in response to contact with APCs that have phagocytosed a yeast-based immunotherapy composition; (5) having immune cells responsive to CTLA4 blockade (e.g., respond to inhibition of CTLA4, such as by anti-CTLA4 antibodies); and/or (6) being more responsive to IDO inhibitors, i.e., the blockade of IDO should ameliorate the suppressive effects of T1IFN-associated IDO activity that impairs Th17 function.

It will be appreciated that sensitivity to T1IFN, when looking at a population, cohort, or group of individuals, will most likely reveal a continuum of responses, i.e., each individual will be more or less sensitive to T1IFN than another individual, resulting in a continuum of sensitivities if one looks at the population, cohort or group as a whole. According to the present invention, the more sensitive an individual is to T1IFN, the more likely he or she will have a meaningful response to yeast-based immunotherapy. The method of the present invention is therefore used in its most general sense to preselect those subjects who are the most likely to respond to yeast-based immunotherapy, which necessarily means that some subjects will be preselected as less likely to respond to yeast-based immunotherapy. The methods will, in some embodiments, have predetermined cutoffs for defining an individual as T1IFN-sensitive or T1IFN-insensitive (e.g., a qualitative or quantitative measure of clinically or biologically meaningful T1IFN-sensitivity, typical of a validated assay). Therefore, some of the subjects preselected as less likely to respond to yeast-based immunotherapy may still display some sensitivity to T1IFN when tested, although not a sufficient response to be categorized as "T1IFN-sensitive". These subjects will be categorized as "T1IFN-insensitive" (or T1IFN-nonresponsive or T1IFN-less responsive) even if they have a minor or low response to T1IFN. While such individuals who are "less likely" to respond to yeast-based immunotherapy based on the T1IFN assay may still achieve some benefit or even great benefit from being treated with this immunotherapy, since the likelihood of benefit is predicted to be lower than for other individuals with greater T1IFN-sensitivity, the decision can be made on an individual basis whether to proceed with yeast-based immunotherapy or instead to try a different type of therapeutic treatment for the disease or condition, which may produce a better outcome. Alternatively, such individuals may be treated with yeast-based immunotherapy in combination with one or more additional agents or therapies that are selected to: (1) improve the ability of the individual to respond to yeast-based immunotherapy based on the now known T1IFN profile of the individual, and/or (2) generally improve the likelihood of a beneficial treatment of the individual given the disease or condition being treated.

The actual decision about whether a subject is T1IFN-sensitive or T1IFN-insensitive is therefore based first on how the individual (or the immune system of the individual) responds to exposure to T1IFN by evaluating a biological sample from the subject before and after exposure to T1IFN (i.e., by comparing a baseline, pre-exposure level of a biomarker to a post-exposure level of the biomarker). In this manner, regardless of the absolute level of the particular biomarker being measured, the test will measure the relative level of the biomarker before and after T1IFN exposure for the individual, which results in a ratio, index, fold-change, or percentage change (or other "Delta" Δ) that can then be compared to a standard. As used herein, reference to any such ratio, index, fold-change, or percentage change (or other "Delta" Δ) is stated with reference to the absolute value of the change. For example, if a biomarker is down-regulated such that the level of the biomarker after T1IFN exposure is one-third the level before exposure, that difference is referred to herein as a ratio of 3 or a three-fold change. As another example, if a biomarker is upregulated such that the level of the biomarker after T1IFN exposure is three times the level before exposure, that difference is referred to herein as a ratio of 3 or a three-fold change. Such a measure is likely to be more informative than by simply comparing absolute levels of a biomarker between different individuals, since the baseline may differ between individuals. Second, the determination of whether the response is considered to indicate sensitivity or insensitivity to T1IFN is most typically based on a predetermined "cutoff" or "standard" for groups of subjects that takes into account the given sample type and type of biomarker(s) screened (and, in some circumstances, the type of disease experienced by the individual). In other words, the ratio, index, fold-change, or percentage change (or other "Delta" Δ) for the individual is then evaluated against a standard or cutoff to classify the individual as T1IFN-sensitive or T1IFN-insensitive. The measure of T1IFN responsiveness may be evaluated differently depending on the type of biological sample tested or the type of biomarker(s) used (e.g., the magnitude of differences in the level of production of a protein that indicate T1IFN sensitivity may be different than magnitude of differential expression of mRNA that indicates sensitivity).

In addition, when more than one T1IFN biomarker is used, they need not be regulated in the same direction. For example, one or more T1IFN biomarkers used in a single assay may respond to T1IFN exposure by being upregulated compared to the baseline level and one or more other T1IFN biomarkers may be downregulated compared to the baseline level. Additionally, when using two or more T1IFN biomarkers, the two or more biomarkers need not be regulated to the same degree or in exactly the same manner to be significant or meaningful for determining the subject's response status. The use of two, three, four, five, six, seven, eight, nine, ten or more T1IFN biomarkers in a single assay may increase the power of the assay, such that individuals who are more likely to respond to yeast-based immunotherapy are more easily identified or distinguished from individuals who are less likely to respond to yeast-based immunotherapy.

T1IFN sensitivity (or insensitivity) is typically determined by measuring, in vivo or ex vivo or in vitro, in a biological sample from an individual, whether the level of a given T1IFN biomarker is changed (upregulated or downregulated, increased or decreased, modified, altered, etc.) after exposure to a T1IFN, as compared to a baseline level of the T1IFN biomarker measured prior to exposure to the T1IFN. If the level of the T1IFN biomarker significantly, substantially, detectably or measurably changes upon exposure to T1IFN and/or according to the cutoff or standard set for the assay, then the individual is sensitive to T1IFN. If the level of the T1IFN biomarker does not change or does not change significantly, substantially, detectably or measurably upon exposure to T1IFN and/or according to the cutoff or standard set for the assay, then the individual is insensitive to T1IFN.

The "level" of the T1IFN biomarker may, for example, be the level of expression if the biomarker is a gene or mRNA (typically measured by detecting mRNA expression), or the level of protein production or expression or localization if the biomarker is a protein, or the level of phosphorylation of a protein if the biomarker is a measure of phosphorylation. Such term will be readily understood by those of skill in the art and is quantified or qualitatively defined based on the type of biomarker and the type of assay used to measure the biomarker.

The "baseline" level of the T1IFN biomarker is measured in vivo or ex vivo or in vitro in the absence of exposure of the biological sample being tested to an exogenous source of T1IFN. A baseline level is preferably an intrinsic baseline level, e.g., a level from a sample that is least impacted by the presence in the individual of a pathogen, or the influence of disease factors in the microenvironment, or even prior administration of T1IFN to the subject. For example, in an HCV-infected individual, it may be preferred to use peripheral blood mononuclear cells (PBMCs) as the sample, rather than hepatocytes, since hepatocytes may still harbor the virus and have a preactivated T1IFN phenotype at baseline. This is not to state that such samples are not suitable, but rather that interpretation of results related to T1IFN sensitivity and the impact of yeast-based immunotherapy may be more informative or different when an intrinsic baseline can be established. Samples obtained from a biopsy, in the case of some diseases, such as cancer or some infectious diseases, are also in useful in some embodiments because such samples may provide information that is specifically relevant to the disease experienced by the individual. Since the goal of the present invention is to preselect patients most likely to respond to yeast-based immunotherapy, which therefore necessarily focuses on the impact of T1IFN on the immune response of an individual, a suitable baseline level is preferably determined using biological samples that comprise immune cells and/or that are most relevant to the intrinsic immune responsiveness of the subject. Baseline levels in a given assay will also typically be adjusted to subtract any "background" or non-specific activity or "noise", in order to improve the accuracy of the detection method.

As discussed above, methods of the invention will, in some embodiments, have predetermined cutoffs or standards for defining an individual as T1IFN-sensitive or T1IFN-insensitive (e.g., a qualitative or quantitative measure of meaningful T1IFN-sensitivity). A predetermined standard may be used to evaluate the change in the T1IFN response (baseline versus post-exposure to T1IFN), the individual can be characterized as T1IFN-sensitive or T1IFN-insensitive, and this phenotype is then used to preselect subjects for treatment with yeast-based immunotherapy (or to choose or offer an alternate treatment protocol for the subject, in the case of T1IFN-insensitive subjects). Predetermined standards for an assay (preselection method) are typically determined in the process of validating an assay, but may also be determined prior to validation based on statistical analysis, and/or retrospective or prospective analysis of groups of subjects and correlations of T1IFN-sensitivity with clinical outcomes associated with yeast-based immunotherapy.

In one embodiment of the invention, the standard for preselecting a subject as T1IFN-sensitive is defined as a change in the level of the T1IFN biomarker, after exposure to T1IFN as compared to pre-exposure (baseline), of at least 3-fold, or at least 4-fold, or at least 5-fold, or at least 6-fold, or at least 7-fold, or at least 8-fold, or at least 9-fold, or at least 10-fold, or at least 11-fold, or at least 12-fold, or at least 13-fold, or at least 14-fold, or at least 15-fold, or at least 16-fold, or at least 17-fold, or at least 18-fold, or at least 19-fold, or at least 20-fold, or at least 25-fold, or at least 30-fold, or at least 40-fold, or at least 50-fold.

In one embodiment of the invention, the ratio of the level of response post-exposure compared to pre-exposure to T1IFN is determined, and the standard for preselecting a subject as T1IFN-sensitive is defined as a ratio of at least 3, at least 4, at least 5, at least 6 at least 7, at least 8, at least 9, at least 10, at least 11, at least 12, at least 13, at least 14, at least 15, at least 16, at least 17, at least 18, at least 19, at least 20, at least 25, at least 30, at least 40, or at least 50.

In one embodiment of the invention, the standard for preselecting a subject as T1IFN-sensitive is defined as a change in the level of the T1IFN biomarker, after exposure to T1IFN as compared to pre-exposure (baseline), of at least 50%, at least 75%, at least 100%, at least 125%, at least 150%, at least 175%, at least 200%, at least 225%, at least 250%, at least 275%, at least 300%, at least 400%, at least 500%, at least 600%, at least 700%.

In one embodiment of the invention, the standard for preselecting a subject as T1IFN-sensitive is defined as a change in the level of the T1IFN biomarker, after exposure to T1IFN as compared to pre-exposure (baseline), that is statistically significant as defined by at least 2 standard errors above median, at least 3 standard errors above median, at least 4 standard errors above median, or at least 5 standard errors above median.

In another embodiment of the invention, the standard for preselecting a subject as T1IFN-sensitive is defined as a change in the level of the T1IFN biomarker, after exposure to T1IFN as compared to pre-exposure (baseline), that is statistically significant as defined by a p-value of $p \leq 0.05$, $p \leq 0.02$, $p \leq 0.01$, $p \leq 0.005$, $p \leq 0.002$, or $p \leq 0.001$.

The method of the invention of preselecting a subject for treatment using yeast-based immunotherapy includes testing a biological sample from the subject for one or more T1IFN biomarkers. As used herein, a biological sample can include any bodily fluid or tissue from a subject that contains cells that can be tested for the responsiveness of the one or more T1IFN biomarkers. Biological samples can include a sample of isolated or partially isolated cells, a tissue sample, a bodily fluid sample, or, for example, a sample of nucleic acids obtained from a cell sample isolated from the patient (e.g., nucleic acids isolated from peripheral blood mononuclear cells (PBMCs)). Tissue samples can be obtained by a biopsy, for example, including by cutting, slicing, swabbing, scraping, or a punch. Bodily fluid samples, which can be obtained by phlebotomy, swabbing, or other simple methods, include, but are not limited to, blood (whole blood or plasma), mucous, and saliva. Preferred cell samples include cells that comprise cells of the immune systems, such as T cells and antigen presenting cells. One type of cell sample that is particularly useful in the present invention is PBMCs. Another type of sample that is particularly useful in the present invention is a biopsy sample.

Methods to determine T1IFN-sensitivity include not only a direct measurement T1IFN and T1IFN response gene products before and after immunotherapy but also the measurement of $CD4^+$ T cell expansion/proliferation defined both in vitro and in vivo. T1IFN-sensitivity and T1IFN-insensitivity (T1IFN-resistance) can be measured by any suitable method known in the art, including those described and exemplified herein. Such methods include, but are not limited to, measurement of T1IFN-responsive genes/proteins as a result of induction by or exposure to T1IFN. Suitable methods for detection of expression and/or levels of genes and proteins include, but are not limited to, polymerase chain reaction (PCR), reverse transcriptase-PCR (RT-PCR), in situ hybridization, Northern blot, sequence analysis, gene microarray analysis, detection of a reporter gene, Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry.

In one aspect, the biological sample is PBMCs, and the T1IFN-sensitivity can be measured using a method selected from ELISA, real-time PCR in a multiplexed PCR reaction, flow cytometry (intracellular cytokine staining), LUMNEX® (multiplex bead-based immunoassay testing platform that simultaneously measures multiple analytes by exciting a sample with a laser, and subsequently analyzing the wavelength of emitted light, Luminex Corporation, Austin, Tex.), or quantitative selected reaction monitoring (SRM)-based mass spectrometry, although the invention is not limited to the use of these particular methods. In one aspect, the biological sample is a biopsy sample, and the T1IFN-sensitivity can be measured using a method selected from Western blot, ELISA, real-time PCR or quantitative SRM-based mass spectrometry, although the invention is not limited to the use of these particular methods.

One exemplary assay suitable for detecting T1IFN sensitivity is to detect the level of expression of a T1IFN-induced protein. In this assay, a cell sample, such as a PBMC sample, is collected from a subject to be tested and either used fresh, or may be frozen and thawed later for testing. Cells are tested for the expression level of the T1IFN-induced protein before exposure to T1IFN in vitro (or ex vivo) and also after exposure to T1IFN and the expression of the protein is quantified by Western blot using an antibody specific for the T1IFN-induced protein. A ratio of post-exposure level to pre-exposure level is calculated. Such an assay for the T1IFN-induced protein, M×A, is described, for example, in Feng et al., 2012, *J Neurol Sci.* 313(1-2):48-53) or a modified version of such an assay is described in the Examples (see Example 1). Other T1IFN-induced proteins can be similarly measured using such an assay.

Another exemplary assay for detecting T1IFN sensitivity is to detect the level of expression of a T1IFN-induced gene, such as by measuring mRNA levels. For example, such an assay for mRNA expression of the T1IFN-induced genes is described in Hundeshagen et al., 2012, supra, Sultanik et al., 2014, supra, Dill et al., 2011, supra, and Kyogoku et al., 2013, supra. In some of these publications, differences before and after exposure to T1IFN ex vivo or in vitro is not evaluated, but the method can be readily adapted to perform this analysis.

Another exemplary assay for detecting T1IFN sensitivity is to detect the level of phosphorylation of a protein that is phosphorylated as a result of activation by T1IFN. Such an assay for phosphorylation of the T1IFN-induced transcription factor, STAT1, is described, for example, in Sultanik et al., 2014, supra.

A potentially accurate way to define T1IFN-sensitivity is by the rapidity with which desensitization occurs when T cells are presented and then shortly thereafter represented with T1IFN. The more sensitive individuals are those who are desensitized to T1IFN at lower doses. In one embodiment of the invention, the sample from the subject is tested a first time for T1IFN-sensitivity, using any of the assays known in the art or described herein, and then the sample is exposed a second time to T1IFN and the measurement of sensitivity is assessed again. Individuals who are highly sensitive to T1IFN are, for some T1IFNs and cell types, desensitized to the T1IFN after the first exposure, resulting in a blunting of the response upon subsequent exposure. Such an assay is described, for example, in Sultanik et al., 2014, supra.

Compositions Useful in the Invention

The yeast-based, antigen-specific immunotherapeutic compositions are unique among various types of immunotherapy, in that these compositions induce innate immune responses, as well as adaptive immune responses that specifically target a variety of disease-associated antigens, including $CD4^+$-dependent, TH17 and TH1 T cell responses and antigen-specific $CD8^+$ T cell responses. Yeast-based immunotherapeutic compositions are administered as biologics or pharmaceutically acceptable compositions. Accordingly, rather than using yeast as an antigen production system followed by purification of the antigen from the yeast, the entire yeast vehicle as described herein must be suitable for, and formulated for, administration to a patient. The yeast-based immunotherapeutic compositions of the invention contain readily detectable yeast DNA and contain substantially more than 5% yeast protein; generally, and dependent on the level of antigen expression by the yeast, yeast-based immunotherapeutics of the invention contain more than 70%, more than 80%, or more than 90% yeast protein.

Yeast-based immunotherapeutic compositions are administered to a patient in order to immunize the patient for therapeutic and/or prophylactic purposes. In one embodiment of the invention, the yeast-based compositions are formulated for administration in a pharmaceutically acceptable excipient or formulation. The composition should be formulated, in one aspect, to be suitable for administration to a human subject (e.g., the manufacturing conditions should be suitable for use in humans, and any excipients or formulations used to finish the composition and/or prepare the dose of the immunotherapeutic for administration should be suitable for use in humans). In one aspect of the invention, yeast-based immunotherapeutic compositions are formulated for administration by injection of the patient or subject, such as by a parenteral route (e.g., by subcutaneous, intraperitoneal, intramuscular or intradermal injection, or another suitable parenteral route).

In conjunction with the yeast vehicle, antigens are most typically expressed as recombinant proteins by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or more antigens are loaded into a yeast vehicle or otherwise complexed with, attached to, mixed with or administered with a yeast vehicle as described herein to form a composition of the present invention. According to the present invention, reference to a "heterologous" protein or "heterologous" antigen, including a heterologous fusion protein, in connection with a yeast vehicle of the invention, means that the protein or antigen is not a protein or antigen that is naturally expressed by the yeast, although a fusion protein that includes heterologous antigen or heterologous protein may also include yeast sequences or proteins or portions thereof that are also naturally expressed by yeast (e.g., an alpha factor prepro sequence as described herein).

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate, or other molecule, or a portion thereof. An antigen may elicit an antigen-specific immune response (e.g., a humoral and/or a cell-mediated immune response) against the same or similar antigens that are encountered by an element of the immune system (e.g., T cells, antibodies).

An antigen can be as small as a single epitope, a single immunogenic domain or larger, and can include multiple epitopes or immunogenic domains. As such, the size of an antigen can be as small as about 8-12 amino acids (i.e., a peptide) and as large as: a full length protein, a multimer, a fusion protein, a chimeric protein, a whole cell, a whole microorganism, or any portions thereof (e.g., lysates of whole cells or extracts of microorganisms). In addition, antigens can include carbohydrates, which can be loaded into a yeast vehicle or into a composition of the invention. It will be appreciated that in some embodiments (e.g., when the antigen is expressed by the yeast vehicle from a recombinant nucleic acid molecule), the antigen is a protein, fusion protein, chimeric protein, or fragment thereof, rather than an entire cell or microorganism.

When the antigen is to be expressed in yeast, an antigen is of a minimum size capable of being expressed recombinantly in yeast, and is typically at least or greater than 25 amino acids in length, or at least or greater than 26, at least or greater than 27, at least or greater than 28, at least or greater than 29, at least or greater than 30, at least or greater than 31, at least or greater than 32, at least or greater than 33, at least or greater than 34, at least or greater than 35, at least or greater than 36, at least or greater than 37, at least or greater than 38, at least or greater than 39, at least or greater than 40, at least or greater than 41, at least or greater than 42, at least or greater than 43, at least or greater than 44, at least or greater than 45, at least or greater than 46, at least or greater than 47, at least or greater than 48, at least or greater than 49, or at least or greater than 50 amino acids in length, or is at least 25-50 amino acids in length, at least 30-50 amino acids in length, or at least 35-50 amino acids in length, or at least 40-50 amino acids in length, or at least 45-50 amino acids in length. Smaller proteins may be expressed, and considerably larger proteins (e.g., hundreds of amino acids in length or even a few thousand amino acids in length) may be expressed. In one aspect, a full-length protein, or a structural or functional domain thereof, or an immunogenic domain thereof, that is lacking one or more amino acids from the N- and/or the C-terminus may be expressed (e.g., lacking between about 1 and about 20 amino acids from the N- and/or the C-terminus). Fusion proteins and chimeric proteins are also antigens that may be expressed in the invention. A "target antigen" is an antigen that is specifically targeted by an immunotherapeutic composition of the invention (i.e., an antigen against which elicitation of an immune response is desired).

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual. In one embodiment, an immunogen elicits a cell-mediated immune response, including a $CD4^+$ T cell response (e.g., TH1, TH2 and/or TH17) and/or a $CD8^+$ T cell response (e.g., a CTL response).

An "immunogenic domain" of a given antigen can be any portion, fragment or epitope of an antigen (e.g., a peptide fragment or subunit or an antibody epitope or other conformational epitope) that contains at least one epitope that acts as an immunogen when administered to an animal. Therefore, an immunogenic domain is larger than a single amino acid and is at least of a size sufficient to contain at least one epitope that can act as an immunogen. For example, a single protein can contain multiple different immunogenic domains. Immunogenic domains need not be linear sequences within a protein, such as in the case of a humoral immune response, where conformational domains are contemplated.

A "functional domain" of a given protein is a portion or functional unit of the protein that includes sequence or structure that is directly or indirectly responsible for at least one biological or chemical function associated with, ascribed to, or performed by the protein. For example, a functional domain can include an active site for enzymatic activity, a ligand binding site, a receptor binding site, a binding site for a molecule or moiety such as calcium, a phosphorylation site, or a transactivation domain.

A "structural domain" of a given protein is a portion of the protein or an element in the protein's overall structure that has an identifiable structure (e.g., it may be a primary or tertiary structure belonging to and indicative of several proteins within a class or family of proteins), is self-stabilizing and/or may fold independently of the rest of the protein. A structural domain is frequently associated with or features prominently in the biological function of the protein to which it belongs.

An epitope is defined herein as a single immunogenic site within a given antigen that is sufficient to elicit an immune response when provided to the immune system in the context of appropriate costimulatory signals and/or activated cells of the immune system. In other words, an epitope is the part of an antigen that is actually recognized by components of the immune system, and may also be referred to as an antigenic determinant. Those of skill in the art will recognize that T cell epitopes are different in size and composition from B cell or antibody epitopes, and that epitopes presented through the Class I MHC pathway differ in size and structural attributes from epitopes presented through the Class II MHC pathway. For example, T cell epitopes presented by Class I MHC molecules are typically between 8 and 11 amino acids in length, whereas epitopes presented by Class II MHC molecules are less restricted in length and may be from 8 amino acids up to 25 amino acids or longer. In addition, T cell epitopes have predicted structural characteristics depending on the specific MHC molecules bound by the epitope. Most antibodies recognize conformational epitopes.

In any of the antigens used in a yeast-based immunotherapeutic composition described herein, including any fusion proteins, the following additional embodiments can apply. First, an N-terminal expression sequence and/or a C-terminal tag are optional, and if used, may be selected from several different sequences described below to improve expression, stability, and/or allow for identification and/or purification of the protein. In one aspect, one or both of the N- or C-terminal sequences are omitted altogether. In addition, many different promoters suitable for use in yeast are known in the art and are encompassed for use to express antigens according to the present invention. Furthermore, short intervening linker sequences (e.g., 1, 2, 3, 4, or 5, or larger, amino acid peptides) may be introduced between portions of the fusion protein for a variety of reasons, including the introduction of restriction enzyme sites to facilitate cloning and future manipulation of the constructs.

As discussed above, optionally, proteins, including fusion proteins, which are used as a component of the yeast-based immunotherapeutic composition of the invention, can be produced using constructs that are particularly useful for improving or enhancing the expression, or the stability of expression, of recombinant antigens in yeast. Typically, the desired antigenic protein(s) or peptide(s) are fused at their amino-terminal (N-terminal) end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, including but not limited to alpha factor, wherein either fusion partner provides improved stability of expression of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, described in more detail herein). In addition, the present invention optionally includes the use of peptides that are fused to the C-terminus of the antigen-encoding construct, particularly for use in the selection and identification of the protein. Such peptides include, but are not limited to, any synthetic or natural peptide, such as a peptide tag (e.g., hexahistidine) or any other short epitope tag. Peptides attached to the C-terminus of an antigen according to the invention can be used with or without the addition of the N-terminal peptides discussed herein.

In one embodiment, a synthetic peptide useful in a fusion protein is linked to the N-terminus of the antigen, the peptide consisting of at least two amino acid residues that are heterologous to the antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid residues at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-6 of the fusion protein is a lysine or an arginine (i.e., the amino acids at positions 2-6, whether part of the synthetic peptide or the protein, if the synthetic peptide is shorter than 5 amino acids, do not include a lysine or an arginine). The synthetic peptide can be as short as two amino acids, but in one aspect, is 2-6 amino acids (including 3, 4, 5 amino acids), and can be longer than 6 amino acids, in whole integers, up to about 200 amino acids, 300 amino acids, 400 amino acids, 500 amino acids, or more.

In one embodiment, a fusion protein comprises an amino acid sequence of M-X2-X3-X4-X5-X6, wherein M is methionine; wherein X2 is any amino acid except glycine, proline, lysine or arginine; wherein X3 is any amino acid except methionine, lysine or arginine; wherein X4 is any amino acid except methionine, lysine or arginine; wherein X5 is any amino acid except methionine, lysine or arginine; and wherein X6 is any amino acid except methionine, lysine or arginine. In one embodiment, the X6 residue is a proline. An exemplary synthetic sequence that enhances the stability of expression of an antigen in a yeast cell and/or prevents post-translational modification of the protein in the yeast includes the sequence M-A-D-E-A-P (SEQ ID NO:1). In addition to the enhanced stability of the expression product, these fusion partners do not appear to negatively impact the immune response against the immunizing antigen in the construct. In addition, the synthetic fusion peptides can be designed to provide an epitope that can be recognized by a selection agent, such as an antibody.

In one embodiment, the antigen is linked at the N-terminus to a yeast protein, such as an alpha factor prepro sequence (also referred to as the alpha factor signal leader sequence. Sequences for yeast alpha factor prepro sequence are known in the art and are encompassed for use in the present invention.

According to any embodiment of the present invention, reference to a "full-length" protein (or a full-length functional domain, a full-length structural domain, or a full-length immunological domain) includes the full-length amino acid sequence of the protein or functional domain, structural domain or immunological domain, as described herein or as otherwise known or described in a publicly available sequence. A protein or domain that is "near full-length", which is also a type of homologue of a protein, differs from a full-length protein or domain, by the addition or deletion or omission of 1, 2, 3, 4, 5, 6, 7, 8, 9, or 10 amino acids from the N- and/or C-terminus of such a full-length protein or full-length domain. General reference to a protein or domain can include both full-length and near full-length proteins, as well as other homologues thereof.

In one aspect, an antigen useful in a yeast-based immunotherapy composition comprises at least 80%, 85%, 90%, 91%, 92%, 93%, 94%, 95%, 96%, 97%, 98%, or 99% of the linear sequence of a full-length protein, or of a functional, structural or immunogenic domain thereof. In one aspect, the antigen is at least 80%, 85%, 90%, 91%, 92%, 93%, 94%, 95%, 96%, 97%, 98%, or 99% identical to a full-length protein, or a functional, structural or immunogenic domain thereof.

In some aspects of the invention, amino acid insertions, deletions, and/or substitutions can be made for one, two, three, four, five, six, seven, eight, nine, ten, or more amino acids of a wild-type or reference protein, provided that the resulting protein, when used as an antigen in a yeast-based immunotherapeutic composition of the invention, elicits an immune response against the target or wild-type or reference protein, which may include an enhanced immune response, a diminished immune response, or a substantially similar immune response. Such antigens can also be referred to herein as "Altered Peptide Ligands" (APLs), which are antigens that may include one or more T cell epitopes, and particularly, cytotoxic T lymphocyte (CTL) epitopes, that have been mutated by substitution of one or more amino acid residues for a different amino acid residue(s). The purpose of the mutation is to elicit a T cell response against the agonist epitope that is enhanced/amplified/improved as compared to the response against the native antigen, which may be achieved by improving the avidity or affinity of the epitope for an MHC molecule or for the T cell receptor that recognizes the epitope in the context of MHC presentation. Antigen agonists may therefore improve the potency or efficiency of a T cell response against native proteins that infect or are expressed by a host.

The invention also includes homologues of any of the above-described fusion proteins, as well as the use of homologues, variants, or mutants of the individual proteins or portions thereof (including any functional and/or immunogenic domains) that are part of such fusion proteins or otherwise described herein. In one aspect, the invention includes the use of fusion proteins or individual (single) proteins or antigens, having amino acid sequences that are at least 85%, 86%, 87%, 88%, 89%, 90%, 91%, 92%, 93%, 94%, 95%, 96%, 97%, 98%, or 99% identical to the amino acid sequence of any one of the fusion proteins or individual proteins or antigens, respectively, over the full length of the fusion protein, or with respect to a defined segment in the fusion protein or a defined protein or domain thereof (immunogenic domain or functional domain (i.e., a domain with at least one biological activity)) that forms part of the fusion protein.

Types of Antigens.

The antigens contemplated for use in this invention include any antigen against which it is desired to elicit an immune response, and in particular, include any antigen for which a therapeutic immune response against such antigen would be beneficial to an individual. For example, the antigens can include, but are not limited to, any antigens associated with a pathogen, including viral antigens, fungal antigens, bacterial antigens, helminth antigens, parasitic antigens, ectoparasite antigens, protozoan antigens, or antigens from any other infectious agent. Antigens can also include any antigens associated with a particular disease or condition, whether from pathogenic or cellular sources, including, but not limited to, cancer antigens, antigens associated with an autoimmune disease (e.g., diabetes antigens), allergy antigens (allergens), mammalian cell molecules harboring one or more mutated amino acids, proteins normally expressed pre- or neo-natally by mammalian cells, proteins whose expression is induced by insertion of an epidemiologic agent (e.g. virus), proteins whose expression is induced by gene translocation, and proteins whose expression is induced by mutation of regulatory sequences. These antigens can be native antigens or genetically engineered antigens which have been modified in some manner (e.g., sequence change or generation of a fusion protein). It will be appreciated that in some embodiments (i.e., when the antigen is expressed by the yeast vehicle from a recombinant nucleic acid molecule), the antigen can be a protein or any epitope or immunogenic domain thereof, a fusion protein, or a chimeric protein, rather than an entire cell or microorganism.

In one aspect of the invention, antigens useful in one or more immunotherapy compositions of the invention include any cancer or tumor-associated antigen. In one aspect, the antigen includes an antigen associated with a preneoplastic or hyperplastic state. The antigen may also be associated with, or causative of cancer. Such an antigen may be tumor-specific antigen, tumor-associated antigen (TAA) or tissue-specific antigen, epitope thereof, and epitope agonist thereof. Cancer antigens include, but are not limited to, antigens from any tumor or cancer, including, but not limited to, melanomas, squamous cell carcinoma, breast cancers, head and neck carcinomas, thyroid carcinomas, soft tissue sarcomas, bone sarcomas, chordomas, testicular cancers, prostatic cancers, ovarian cancers, bladder cancers, skin cancers, brain cancers, angiosarcomas, hemangiosarcomas, mast cell tumors, leukemias, lymphomas, primary hepatic cancers, lung cancers, pancreatic cancers, gastrointestinal cancers (including colorectal cancers), renal cell carcinomas, hematopoietic neoplasias and metastatic cancers thereof.

Suitable cancer antigens include but are not limited to carcinoembryonic antigen (CEA) and epitopes thereof such as CAP-1, CAP-1-6D (GenBank Accession No. M29540), MART-1 (Kawakami et al, J. Exp. Med. 180:347-352, 1994), MAGE-1 (U.S. Pat. No. 5,750,395), MAGE-3, GAGE (U.S. Pat. No. 5,648,226), GP-100 (Kawakami et al Proc. Nat'l Acad. Sci. USA 91:6458-6462, 1992), MUC-1, MUC-2, point mutated Ras oncoprotein, normal and point mutated p53 oncoproteins (Hollstein et al Nucleic Acids Res. 22:3551-3555, 1994), PSMA (Israeli et al Cancer Res. 53:227-230, 1993), tyrosinase (Kwon et al PNAS 84:7473-7477, 1987), TRP-1 (gp75) (Cohen et al Nucleic Acid Res. 18:2807-2808, 1990; U.S. Pat. No. 5,840,839), NY-ESO-1 (Chen et al PAS 94: 1914-1918, 1997), TRP-2 (Jackson et al EMBOJ, 11:527-535, 1992), TAG72, KSA, CA-125, PSA, HER-2/neu/c-erb/B2, (U.S. Pat. No. 5,550,214), EGFR, hTERT, p'73, B-RAF, adenomatous polyposis coli (APC), Myc, von Hippel-Lindau protein (VHL), Rb-1, Rb-2, androgen receptor (AR), Smad4, MDR1, Flt-3, BRCA-1, BRCA-2, Bcr-Abl, pax3-fkhr, ews-fli-1, Brachyury, HERV-H, HERV-K, TWIST, Mesothelin, NGEP, modifications of such antigens and tissue specific antigens, splice variants of such antigens, and/or epitope agonists of such antigens. Other cancer antigens are known in the art. Other cancer antigens may also be identified, isolated and cloned by methods known in the art such as those disclosed in U.S. Pat. No. 4,514,506. Cancer antigens may also include one or more growth factors and splice variants of each.

In one aspect of the invention, antigens useful in one or more immunotherapy compositions of the invention include any antigens associated with a pathogen or a disease or condition caused by or associated with a pathogen, including, but not limited to, an infectious disease. Such antigens include, but are not limited to, any antigens associated with a pathogen, including viral antigens, fungal antigens, bacterial antigens, helminth antigens, parasitic antigens, ectoparasite antigens, protozoan antigens, or antigens from any other infectious agent.

In one aspect, the antigen is from virus, including, but not limited to, adenoviruses, arena viruses, bunyaviruses, coronaviruses, coxsackie viruses, cytomegaloviruses, Epstein-Barr viruses, flaviviruses, hepadnaviruses, hepatitis viruses (e.g., HBV, HCV, HDV), herpes viruses, influenza viruses, lentiviruses (e.g., HIV), measles viruses, mumps viruses, myxoviruses, orthomyxoviruses, papilloma viruses, papovaviruses, parainfluenza viruses, paramyxoviruses, parvoviruses, picornaviruses, pox viruses, rabies viruses, respiratory syncytial viruses, reoviruses, rhabdoviruses, rubella viruses, togaviruses, and varicella viruses.

In another aspect, the antigen is from an infectious agent from a genus selected from: *Aspergillus, Bordatella, Brugia, Candida, Chlamydia, Coccidia, Cryptococcus, Dirofilaria, Escherichia, Francisella, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma, Vibriocholerae*, and *Yersinia*.

In one aspect, the antigen is from a bacterium from a family selected from: Enterobacteriaceae, Micrococcaceae, Vibrionaceae, Pasteurellaceae, Mycoplasmataceae, and Rickettsiaceae. In one aspect, the bacterium is of a genus selected from: *Pseudomonas, Bordetella, Mycobacterium, Vibrio, Bacillus, Salmonella, Francisella, Staphylococcus, Streptococcus, Escherichia, Enterococcus, Pasteurella*, and *Yersinia*. In one aspect, the bacterium is from a species selected from: *Pseudomonas aeruginosa, Pseudomonas mallei, Pseudomonas pseudomallei, Bordetella pertussis, Mycobacterium tuberculosis, Mycobacterium leprae, Francisella tularensis, Vibrio cholerae, Bacillus anthracis, Salmonella enteric, Yersinia pestis, Escherichia coli* and *Bordetella bronchiseptica.*

In one aspect, the antigen is from a fungus, such a fungus including, but not limited to, a fungus from *Saccharomyces* spp., *Aspergillus* spp., *Cryptococcus* spp., *Coccidioides* spp., *Neurospora* spp., *Histoplasma* spp., or *Blastomyces* spp. In one aspect, the fungus is from a species selected from: *Aspergillus fumigatus, A. flavus, A. niger, A. terreus, A. nidulans, Coccidioides immitis, Coccidioides posadasii* or *Cryptococcus neoformans.*

Yeast-Based Immunotherapy Compositions.

In various embodiments of the invention, the invention includes the use of at least one "yeast-based immunotherapeutic composition" (which phrase may be used interchangeably with "yeast-based immunotherapy product", "yeast-based immunotherapy composition", "yeast-based composition", "yeast-based immunotherapeutic", "yeast-based vaccine", or derivatives of these phrases). An "immunotherapeutic composition" is a composition that elicits an immune response sufficient to achieve at least one therapeutic benefit in a subject. As used herein, yeast-based immunotherapeutic composition refers to a composition that includes a yeast vehicle component and that elicits an immune response sufficient to achieve at least one therapeutic benefit in a subject. More particularly, a yeast-based immunotherapeutic composition is a composition that includes a yeast vehicle component and can elicit or induce an immune response, such as a cellular immune response, including without limitation a T cell-mediated cellular immune response. In one aspect, a yeast-based immunotherapeutic composition useful in the invention is capable of inducing a $CD8^+$ and/or a $CD4^+$ T cell-mediated immune response and in one aspect, a $CD8^+$ and a $CD4^+$ T cell-mediated immune response. Optionally, a yeast-based immunotherapeutic composition is capable of eliciting a humoral immune response.

Yeast-based immunotherapy compositions of the invention may be either "prophylactic" or "therapeutic". When provided prophylactically, the compositions of the present invention are provided in advance of any symptom of infection or disease. Such a composition could be administered at birth, in early childhood, or to adults, particularly adults who may be at higher risk of a disease or condition amenable to use of immunotherapy. The prophylactic administration of the immunotherapy compositions serves to prevent subsequent infection or disease, to resolve an infection or disease more quickly or more completely if infection or disease subsequently ensues, and/or to ameliorate the symptoms of infection or disease if infection or disease subsequently ensues. When provided therapeutically, the immunotherapy compositions are provided at or after the onset of infection or disease, with the goal of ameliorating at least one symptom of the infection or disease and preferably, with a goal of eliminating the infection or disease, providing a long lasting remission of infection or disease, and/or providing long term immunity against subsequent infection or disease.

Typically, a yeast-based immunotherapy composition includes a yeast vehicle and at least one antigen or immunogenic domain thereof expressed by, attached to, or mixed with the yeast vehicle, wherein the antigen is heterologous to the yeast, and wherein the antigen comprises one or more antigens or immunogenic domains thereof. In some embodiments, the antigen or immunogenic domain thereof is provided as a fusion protein. In one aspect of the invention, fusion protein can include two or more antigens. In one aspect, the fusion protein can include two or more immunogenic domains of one or more antigens, or two or more epitopes of one or more antigens.

In any of the yeast-based immunotherapy compositions used in the present invention, the following aspects related to the yeast vehicle are included in the invention. According to the present invention, a yeast vehicle is any yeast cell (e.g., a whole or intact cell) or a derivative thereof (see below) that can be used in conjunction with one or more antigens, immunogenic domains thereof or epitopes thereof in a therapeutic composition of the invention, or in one aspect, the yeast vehicle can be used alone or as an adjuvant. The yeast vehicle can therefore include, but is not limited to, a live intact (whole) yeast microorganism (i.e., a yeast cell having all its components including a cell wall), a killed (dead) or inactivated intact yeast microorganism, or derivatives of intact/whole yeast including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., 1991, *Meth. Enzymol.* 194, 662-674., incorporated herein by reference in its entirety.

Yeast cytoplasts are typically produced by enucleation of yeast cells. Such a method is described, for example, in Coon, 1978, *Natl. Cancer Inst. Monogr.* 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane.

An example of a yeast cell wall preparation is a preparation of isolated yeast cell walls carrying an antigen on its surface or at least partially embedded within the cell wall such that the yeast cell wall preparation, when administered to an animal, stimulates a desired immune response against a disease target.

Any yeast strain can be used to produce a yeast vehicle of the present invention. Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains).

Genera of yeast strains that may be used in the invention include but are not limited to *Saccharomyces, Candida, Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in one aspect, yeast genera are selected from *Saccharomyces, Hansenula*, and *Pichia*, and in one aspect, *Saccharomyces* is used. Species of yeast strains that may be used in the invention include but are not limited to *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe. S. cerevisiae* is useful as it is relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain. The *S. cerevisiae* strain is one such strain that is capable of supporting expression vectors that allow one or more target antigen(s) and/or antigen fusion protein(s) and/or other proteins to be expressed at high levels. In addition, any mutant yeast strains can be used in the present invention, including those that exhibit reduced post-translational modifications of expressed target antigens or other proteins, such as mutations in the enzymes that extend N-linked glycosylation.

In most embodiments of the invention, the yeast-based immunotherapy composition includes at least one antigen, immunogenic domain thereof, or epitope thereof. The antigens contemplated for use in this invention include antigen against which it is desired to elicit an immune response for the purpose of prophylactically or therapeutically immunizing a host against infection or disease.

In one aspect of the invention, the yeast vehicle is manipulated such that the antigen is expressed or provided by delivery or translocation of an expressed protein product, partially or wholly, on the surface of the yeast vehicle (extracellular expression). One method for accomplishing this aspect of the invention is to use a spacer arm for positioning one or more protein(s) on the surface of the yeast vehicle. For example, one can use a spacer arm to create a fusion protein of the antigen(s) or other protein of interest with a protein that targets the antigen(s) or other protein of interest to the yeast cell wall. For example, one such protein that can be used to target other proteins is a yeast protein (e.g., cell wall protein 2 (cwp2), Aga2, Pir4 or Flo1 protein) that enables the antigen(s) or other protein to be targeted to the yeast cell wall such that the antigen or other protein is located on the surface of the yeast. Proteins other than yeast proteins may be used for the spacer arm; however, for any spacer arm protein, it is most desirable to have the immunogenic response be directed against the target antigen rather than the spacer arm protein. As such, if other proteins are used for the spacer arm, then the spacer arm protein that is used should not generate such a large immune response to the spacer arm protein itself such that the immune response to the target antigen(s) is overwhelmed. One of skill in the art should aim for a small immune response to the spacer arm protein relative to the immune response for the target antigen(s). Spacer arms can be constructed to have cleavage sites (e.g., protease cleavage sites) that allow the antigen to be readily removed or processed away from the yeast, if desired. Any known method of determining the magnitude of immune responses can be used (e.g., antibody production, lytic assays, etc.) and are readily known to one of skill in the art.

Another method for positioning the target antigen(s) or other proteins to be exposed on the yeast surface is to use signal sequences such as glycosylphosphatidyl inositol (GPI) to anchor the target to the yeast cell wall. Alternatively, positioning can be accomplished by appending signal sequences that target the antigen(s) or other proteins of interest into the secretory pathway via translocation into the endoplasmic reticulum (ER) such that the antigen binds to a protein which is bound to the cell wall (e.g., cwp).

In one aspect, the spacer arm protein is a yeast protein. The yeast protein can consist of between about two and about 800 amino acids of a yeast protein. In one embodiment, the yeast protein is about 10 to 700 amino acids. In another embodiment, the yeast protein is about 40 to 600 amino acids. Other embodiments of the invention include the yeast protein being at least 250 amino acids, at least 300 amino acids, at least 350 amino acids, at least 400 amino acids, at least 450 amino acids, at least 500 amino acids, at least 550 amino acids, at least 600 amino acids, or at least 650 amino acids. In one embodiment, the yeast protein is at least 450 amino acids in length. Another consideration for optimizing antigen surface expression, if that is desired, is whether the antigen and spacer arm combination should be expressed as a monomer or as dimer or as a trimer, or even more units connected together. This use of monomers, dimers, timers, etc. allows for appropriate spacing or folding of the antigen such that some part, if not all, of the antigen is displayed on the surface of the yeast vehicle in a manner that makes it more immunogenic.

Use of yeast proteins can stabilize the expression of fusion proteins in the yeast vehicle, prevents posttranslational modification of the expressed fusion protein, and/or targets the fusion protein to a particular compartment in the yeast (e.g., to be expressed on the yeast cell surface). For delivery into the yeast secretory pathway, exemplary yeast proteins to use include, but are not limited to: Aga (including, but not limited to, Aga1 and/or Aga2); SUC2 (yeast invertase); alpha factor signal leader sequence; CPY; Cwp2p for its localization and retention in the cell wall; BUD genes for localization at the yeast cell bud during the initial phase of daughter cell formation; Flo1p; Pir2p; and Pir4p.

Other sequences can be used to target, retain and/or stabilize the protein to other parts of the yeast vehicle, for example, in the cytosol or the mitochondria or the endoplasmic reticulum or the nucleus. Examples of suitable yeast protein that can be used for any of the embodiments above include, but are not limited to, TK, AF, SEC7; phosphoenolpyruvate carboxykinase PCK1, phosphoglycerokinase PGK and triose phosphate isomerase TPI gene products for their repressible expression in glucose and cytosolic localization; the heat shock proteins SSA1, SSA3, SSA4, SSC1, whose expression is induced and whose proteins are more thermostable upon exposure of cells to heat treatment; the mitochondrial protein CYC1 for import into mitochondria; ACT1.

Methods of producing yeast vehicles and expressing, combining and/or associating yeast vehicles with antigens and/or other proteins and/or agents of interest to produce yeast-based immunotherapy compositions are contemplated by the invention.

According to the present invention, the term "yeast vehicle-antigen complex" or "yeast-antigen complex" is used generically to describe any association of a yeast vehicle with an antigen, and can be used interchangeably with "yeast-based immunotherapy composition" when such composition is used to elicit an immune response as described above. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transfected with a heterologous nucleic acid molecule encoding a protein (e.g., the antigen) such that the protein is expressed by the yeast cell. Such a yeast is also referred to herein as a recombinant yeast or a recombinant yeast vehicle. The yeast cell can then be loaded into the dendritic cell as an intact cell, or the yeast cell can be killed, or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen or other protein.

In general, the yeast vehicle and antigen(s) and/or other agents can be associated by any technique described herein. In one aspect, the yeast vehicle was loaded intracellularly with the antigen(s) and/or agent(s). In another aspect, the antigen(s) and/or agent(s) was covalently or non-covalently attached to the yeast vehicle. In yet another aspect, the yeast vehicle and the antigen(s) and/or agent(s) were associated by mixing. In another aspect, and in one embodiment, the antigen(s) and/or agent(s) is expressed recombinantly by the yeast vehicle or by the yeast cell or yeast spheroplast from which the yeast vehicle was derived.

A number of antigens and/or other proteins to be produced by a yeast vehicle of the present invention is any number of antigens and/or other proteins that can be reasonably produced by a yeast vehicle, and typically ranges from at least one to at least about 6 or more, including from about 2 to about 6 heterologous antigens and or other proteins.

Expression of an antigen or other protein in a yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art.

Promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SEC7) and acid phosphatase (PHO5), including hybrid promoters such as ADH2/GAPDH and CYC1/

GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule can be introduced into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

Effective conditions for the production of recombinant yeast vehicles and expression of the antigen and/or other protein by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, Methods in Enzymology, vol. 194, Academic Press, San Diego).

In some embodiments of the invention, yeast are grown under neutral pH conditions. As used herein, the general use of the term "neutral pH" refers to a pH range between about pH 5.5 and about pH 8, and in one aspect, between about pH 6 and about 8. (described in detail in PCT Publication No. WO 2008/097863).

In one embodiment, control of the amount of yeast glycosylation is used to control the expression of antigens by the yeast, particularly on the surface. The amount of yeast glycosylation can affect the immunogenicity and antigenicity of the antigen expressed on the surface, since sugar moieties tend to be bulky. As such, the existence of sugar moieties on the surface of yeast and its impact on the three-dimensional space around the target antigen(s) should be considered in the modulation of yeast according to the invention. Any method can be used to reduce the amount of glycosylation of the yeast (or increase it, if desired). For example, one could use a yeast mutant strain that has been selected to have low glycosylation (e.g., mnn1, och1 and mnn9 mutants), or one could eliminate by mutation the glycosylation acceptor sequences on the target antigen. Alternatively, one could use a yeast with abbreviated glycosylation patterns, e.g., Pichia. One can also treat the yeast using methods that reduce or alter the glycosylation.

In one embodiment of the present invention, as an alternative to expression of an antigen or other protein recombinantly in the yeast vehicle, a yeast vehicle is loaded intracellularly with the protein or peptide, or with carbohydrates or other molecules that serve as an antigen and/or are useful as immunomodulatory agents or biological response modifiers according to the invention. Subsequently, the yeast vehicle, which now contains the antigen and/or other proteins intracellularly, can be administered to an individual or loaded into a carrier such as a dendritic cell. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom. Any number of antigens and/or other agents can be loaded into a yeast vehicle in this embodiment, from at least 1, 2, 3, 4 or any whole integer up to hundreds or thousands of antigens and/or other agents, such as would be provided by the loading of a microorganism or portions thereof, for example.

In another embodiment of the present invention, an antigen and/or other agent is physically attached to the yeast vehicle. Physical attachment of the antigen and/or other agent to the yeast vehicle can be accomplished by any method suitable in the art, including covalent and non-covalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

In one embodiment of the invention, the yeast vehicle and the antigen or other protein are both loaded intracellularly into a carrier such as a dendritic cell or macrophage to form the therapeutic composition or vaccine of the present invention. Alternatively, an antigen or other protein can be loaded into a dendritic cell in the absence of the yeast vehicle.

In one embodiment, intact yeast (with or without expression of heterologous antigens or other proteins) can be ground up or processed in a manner to produce yeast cell wall preparations, yeast membrane particles or yeast fragments (i.e., not intact) and the yeast fragments can, in some embodiments, be provided with or administered with other compositions that include antigens (e.g., DNA vaccines, protein subunit vaccines, killed or inactivated pathogens) to enhance immune responses. For example, enzymatic treatment, chemical treatment or physical force (e.g., mechanical shearing or sonication) can be used to break up the yeast into parts that are used as an adjuvant.

In one embodiment of the invention, yeast vehicles useful in the invention include yeast vehicles that have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods. See, for example, the methodology disclosed in standard yeast culturing textbooks such as *Methods of Enzymology*, Vol. 194, Cold Spring Harbor Publishing (1990). Any of the inactivation strategies used should take the secondary, tertiary or quaternary structure of the target antigen into consideration and preserve such structure as to optimize its immunogenicity.

Yeast vehicles can be formulated into yeast-based immunotherapy compositions or products of the present invention, including preparations to be administered to a subject directly or first loaded into a carrier such as a dendritic cell, using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

In one embodiment of the present invention, a composition can include additional agents, which may also be referred to as biological response modifier compounds, or the ability to produce such agents/modifiers. For example, a yeast vehicle can be transfected with or loaded with at least one antigen and at least one agent/biological response modifier compound, or a composition of the invention can be administered in conjunction with at least one agent/biological response modifier. Biological response modifiers include adjuvants and other compounds that can modulate immune responses, which may be referred to as immunomodulatory compounds, as well as compounds that modify the biological activity of another compound or agent, such as a yeast-based immunotherapeutic, such biological activity not being limited to immune system effects. Certain immunomodulatory compounds can stimulate a protective immune response whereas others can suppress a harmful immune response, and whether an immunomodulatory is useful in combination with a given yeast-based immunotherapeutic may depend, at least in part, on the disease state or condition to be treated or prevented, and/or on the individual who is to be treated. Certain biological response modifiers preferentially enhance a cell-mediated immune response whereas others preferentially enhance a humoral immune response (i.e., can stimulate an immune response in which there is an increased level of cell-mediated compared to humoral immunity, or vice versa.). Certain biological response modifiers have one or more properties in common with the biological properties of yeast-based immunotherapeutics or enhance or complement the biological properties of yeast-based immunotherapeutics. There are a number of techniques known to those skilled in the art to measure stimulation or suppression of immune responses, as well as to differentiate cell-mediated immune responses from humoral immune responses, and to differentiate one type of cell-mediated response from another (e.g., a TH17 response versus a TH1 response).

Agents/biological response modifiers useful in the invention may include, but are not limited to, cytokines, chemokines, hormones, lipidic derivatives, peptides, proteins, polysaccharides, small molecule drugs, antibodies and antigen binding fragments thereof (including, but not limited to, anti-cytokine antibodies, anti-cytokine receptor antibodies, anti-chemokine antibodies), vitamins, polynucleotides, nucleic acid binding moieties, aptamers, and growth modulators. Any combination of such agents is contemplated by the invention, and any of such agents combined with or administered in a protocol with (e.g., concurrently, sequentially, or in other formats with) a yeast-based immunotherapeutic is a composition encompassed by the invention. Such agents are well known in the art. These agents may be used alone or in combination with other agents described herein.

Agents can include agonists and antagonists of a given protein or peptide or domain thereof. As used herein, an "agonist" is any compound or agent, including without limitation small molecules, proteins, peptides, antibodies, nucleic acid binding agents, etc., that binds to a receptor or ligand and produces or triggers a response, which may include agents that mimic the action of a naturally occurring substance that binds to the receptor or ligand. An "antagonist" is any compound or agent, including without limitation small molecules, proteins, peptides, antibodies, nucleic acid binding agents, etc., that blocks or inhibits or reduces the action of an agonist.

Compositions of the invention can further include or can be administered with (concurrently, sequentially, or intermittently with) any other compounds or compositions that are useful for preventing or treating an infection, disease or condition, or any compounds that treat or ameliorate any symptom of the infection, disease or condition.

The invention also includes a kit comprising any of the compositions described herein, or any of the individual components of the compositions described herein.

Methods for Administration or Use of Compositions of the Invention

One embodiment of the present invention relates to a method to treat a subject with yeast-based immunotherapy, which includes administering a yeast-based immunotherapy composition to a subject who has been preselected as being sensitive to T1IFN. Another embodiment of the present invention relates to a method to treat a subject with yeast-based immunotherapy, including the steps of: (a) preselecting a subject who is sensitive to T1IFN; and (b) administering yeast-based immunotherapy to the subject. Another embodiment of the present invention relates to a method to treat cancer or a disease caused by a pathogen (which can include an infectious disease) with yeast-based immunotherapy. The method includes administering a yeast-based immunotherapy composition to a subject who has cancer or a disease caused by a pathogen, whose level of one or more T1IFN-regulated biomarkers changes significantly, substantially, detectably or measurably as a result of contacting T1IFN-naïve peripheral blood mononuclear cells (PBMCs) from the subject ex vivo or in vitro with T1IFN.

In one aspect, the level of one or more T1IFN-regulated biomarkers changes, after exposure to T1IFN as compared to pre-exposure (baseline), at least 3-fold, or at least 4-fold, or at least 5-fold, or at least 6-fold, or at least 7-fold, or at least 8-fold, or at least 9-fold, or at least 10-fold, or at least 11-fold, or at least 12-fold, or at least 13-fold, or at least 14-fold, or at least 15-fold, or at least 16-fold, or at least 17-fold, or at least 18-fold, or at least 19-fold, or at least 20-fold, or at least 25-fold, or at least 30-fold, or at least 40-fold, or at least 50-fold. In one aspect, the ratio of the level of response post-exposure compared to pre-exposure to T1IFN is at least 3, at least 4, at least 5, at least 6 at least 7, at least 8, at least 9, at least 10, at least 11, at least 12, at least 13, at least 14, at least is, at least 16, at least 17, at least 18 at least 19, at least 20, at least 25, at least 30, at least 40, or at least 50. In one aspect, the level of one or more T1IFN-regulated biomarkers changes, after exposure to T1IFN as compared to pre-exposure (baseline), at least 50%, at least 75%, at least 100%, at least 125%, at least 150%, at least 175%, at least 200%, at least 225%, at least 250%, at least 275%, at least 300%, at least 400%, at least 500%, at least 600%, at least 700%. In one aspect, the change in the level of the T1IFN biomarker, after exposure to T1IFN as compared to pre-exposure (baseline), that is statistically significant as defined by at least 2 standard errors above median, at least 3 standard errors above median, at least 4 standard errors above median, or at least 5 standard errors above median. In another aspect, the change in the level of one or more T1IFN-regulated biomarkers changes, after exposure to T1IFN as compared to pre-exposure (baseline), is statistically significant as defined by a p-value of $p=0.05$, $p=0.02$, $p=0.01$, $p=0.005$, $p=0.002$, or $p=0.001$.

In the embodiment of the present invention related to a method to treat a subject with yeast-based immunotherapy, the method to preselect or analyze the subject (individual) for being sensitive to T1IFN can be conducted according to any of the methods for measuring T1IFN-sensitivity (or T1IFN-insensitivity) described herein. Such methods are described in detail above, and are also exemplified in the Examples.

Compositions useful in the invention, which can include any one or more (e.g., combinations of two, three, four, five, or more) yeast-based immunotherapeutic compositions described herein, can be used in a variety of in vivo and in vitro methods, including, but not limited to, to treat and/or prevent an infection, disease or condition and/or its sequelae.

As used herein, the phrase "treat" an infection, disease or condition, or any permutation thereof (e.g., "treated for infection", etc.) generally refers to applying or administering a composition of the invention once the infection, disease or condition (acute or chronic) has occurred, with the goal of reduction or elimination of at least one symptom resulting from the infection, disease or condition in the individual, delaying or preventing the onset and/or severity of symptoms and/or downstream sequelae caused by the infection, disease or condition, reduction of organ or physiological system damage resulting from the infection, disease or condition, improvement of immune responses against the infection, disease or condition, improvement of long term memory immune responses against the infection, disease or condition, and/or improved general health of the individual or population of individuals.

To "prevent" an infection, disease or condition, or any permutation thereof (e.g., "prevention of infection", etc.), generally refers to applying or administering a composition of the invention before an infection, disease or condition has occurred, with the goal of preventing the infection, disease or condition, or, should the infection, disease or condition later occur, at least reducing the severity, and/or length of infection, disease or condition and/or the physiological damage caused by the infection, disease or condition, including preventing or reducing the severity or incidence of at least one symptom resulting from the infection, disease or condition in the individual, and/or delaying or preventing the onset and/or severity of symptoms and/or downstream sequelae caused by the infection, disease or condition, in an individual or population of individuals.

The present invention includes the delivery (administration, immunization) of one or more immunotherapeutic compositions of the invention, including a yeast-based immunotherapy composition, to a subject. The administration process can be performed ex vivo or in vivo, but is typically performed in vivo. Ex vivo administration refers to performing part of the regulatory step outside of the patient, such as administering a composition of the present invention to a population of cells (dendritic cells) removed from a patient under conditions such that a yeast vehicle, antigen(s) and any other agents or compositions are loaded into the cell, and returning the cells to the patient. The therapeutic composition of the present invention can be returned to a patient, or administered to a patient, by any suitable mode of administration.

Administration of a composition can be systemic, mucosal and/or proximal to the location of the target site (e.g., near a site of infection). Suitable routes of administration will be apparent to those of skill in the art, depending on the type of condition to be prevented or treated, the antigen used, and/or the target cell population or tissue.

Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992). Other routes of administration that modulate mucosal immunity may be useful in the treatment of viral infections. Such routes include bronchial, intradermal, intramuscular, intranasal, other inhalatory, rectal, subcutaneous, topical, transdermal, vaginal and urethral routes. In one aspect, an immunotherapeutic composition of the invention is administered subcutaneously.

With respect to the yeast-based immunotherapy compositions of the invention, in general, a suitable single dose is a dose that is capable of effectively providing a yeast vehicle and an antigen (if included) to a given cell type, tissue, or region of the patient body in an amount effective to elicit an antigen-specific immune response against one or more target antigens or epitopes, when administered one or more times over a suitable time period. For example, in one embodiment, a single dose of a yeast vehicle of the present invention is from about $1\times10^5$ to about $5\times10^7$ yeast cell equivalents per kilogram body weight of the organism being administered the composition. In one aspect, a single dose of a yeast vehicle of the present invention is from about 0.1 Y.U. ($1\times10^6$ cells) to about 100 Y.U. ($1\times10^9$ cells) per dose (i.e., per organism), including any interim dose, in increments of $0.1\times10^6$ cells (i.e., $1.1\times10^6$, $1.2\times10^6$, $1.3\times10^6$ . . . ). In one embodiment, doses include doses between 1 Y.U and 40 Y.U., doses between 1 Y.U. and 50 Y.U., doses between 1 Y.U. and 60 Y.U., doses between 1 Y.U. and 70 Y.U., or doses between 1 Y.U. and 80 Y.U., and in one aspect, between 10 Y.U. and 40 Y.U., 50 Y.U., 60 Y.U., 70 Y.U., or 80 Y.U. In one embodiment, the doses are administered at different sites on the individual but during the same dosing period. For example, a 40 Y.U. dose may be administered via by injecting 10 Y.U. doses to four different sites on the individual during one dosing period, or a 20 Y.U. dose may be administered by injecting 5 Y.U. doses to four different sites on the individual, or by injecting 10 Y.U. doses to two different sites on the individual, during the same dosing period. The invention includes administration of an amount of the yeast-based immunotherapy composition (e.g., 1, 2, 3, 4, 5, 6, 7, 8, 9 10, 11, 12, 13, 14, 15, 16, 17, 18, 19, 20 Y.U. or more) at 1, 2, 3, 4, 5, 6, 7, 8, 9, 10, or more different sites on an individual to form a single dose.

"Boosters" or "boosts" of a therapeutic composition are administered, for example, when the immune response against the antigen has waned or as needed to provide an immune response or induce a memory response against a particular antigen or antigen(s). Boosters can be administered from about 1, 2, 3, 4, 5, 6, 7, or 8 weeks apart, to monthly, to bimonthly, to quarterly, to annually, to several years after the original administration. In one embodiment, an administration schedule is one in which from about $1\times10^5$ to about $5\times10^7$ yeast cell equivalents of a composition per kg body weight of the organism is administered at least 1, 2, 3, 4, 5, 6, 7, 8, 9, 10, or more times over a time period of from weeks, months, or years. In one embodiment, the doses are administered weekly for 1, 2, 3, 4, 5, 6, 7, 8, 9, 10 or more doses, followed by monthly doses as needed to achieve the desired therapeutic or prophylactic effect. In one embodiment, the doses are administered in a 4-weekly protocol (every 4 weeks, or on day 1, week 4, week 8, week 12, etc., for between 2 and 10 doses or longer as determined by the clinician).

With respect to administration of yeast-based immunotherapeutic compositions described herein, a single composition can be administered to an individual or population of individuals or combination of such compositions can be administered. Accordingly, two or more compositions can be selected in a "spice rack" approach to most effectively prevent or treat an infection, disease or condition in a given individual or population of individuals.

In one aspect of the invention, one or more additional therapeutic agents are administered sequentially with the yeast-based immunotherapy composition. In another embodiment, one or more additional therapeutic agents are administered before the yeast-based immunotherapy composition is administered. In another embodiment, one or more additional therapeutic agents are administered after the yeast-based immunotherapy composition is administered. In one embodiment, one or more additional therapeutic agents are administered in alternating doses with the yeast-based immunotherapy composition, or in a protocol in which the yeast-based composition is administered at prescribed intervals in between or with one or more consecutive doses of the additional agents, or vice versa. In one embodiment, the yeast-based immunotherapy composition is administered in one or more doses over a period of time prior to commencing the administration of the additional agents. In other words, the yeast-based immunotherapeutic composition is administered as a monotherapy for a period of time, and then the agent administration is added, either concurrently with new doses of yeast-based immunotherapy, or in an alternating fashion with yeast-based immunotherapy. Alternatively, the agent may be administered for a period of time prior to beginning administration of the yeast-based immunotherapy composition. In one aspect, the yeast is engineered to express or carry the agent, or a different yeast is engineered or produced to express or carry the agent.

Agents/biological response modifiers that are particularly useful in combination with a yeast-based immunotherapy composition in accordance with the invention include, but are not limited to: STING agonists, STING antagonists, anti-T1IFN antibodies, anti-CD40 antibody, CD40L, lymphocyte-activation gene 3 (LAG3) protein and/or IMP321 (T-cell immunostimulatory factor derived from the soluble form of LAG3); T cell co-stimulators (e.g., anti-CD137, anti-CD28, anti-CD40 antibodies); alemtuzumab (e.g., CamPath®), denileukin diftitox (e.g., ONTAK®); anti-CD4 antibody; anti-CD25 antibody; immune checkpoint inhibitors (e.g., inhibitors of "immune checkpoints" which are inhibitory pathways of the immune system that maintain self-tolerance and modulate the duration and amplitude of physiological immune responses, such immune checkpoint inhibitors including but not limited to: anti-CTLA-4 antibody, such as ipilimumab (Bristol-Myers Squibb, Princeton, N.J.) or tremelimumab (MedImmune/AstraZeneca, Wilmington, Del.), programmed cell death protein 1 (PD-1), programmed cell death protein 1 ligand (PD-L1), programmed cell death protein 2 ligand (PD-L2, such as the PD-L2 fusion protein known as AMP-224 (Amplimmune, Gaithersburg, Md./GlaxoSmithKline, Philadelphia, Pa.)), anti-PD-1 antibody (such as nivolumab (Bristol-Myers Squibb), pembrolizumanb (Merck, Whitehouse Station, N.J.), or pidilizumab (CureTech, Yavne, Israel)), anti-PD-Li antibody (such as MPDL3280A (Genentech, South San Francisco, Calif.), MEDI4736 (MedImmune/AstraZeneca), BMS-936559 (Bristol-Myers Squibb), MSB0010718C (EMD Serono, Rockland, Md.)), or anti-PD-L2 antibody); indoleamine 2,3-dioxygenase (IDO) inhibitors (such as INCB24360); agents that block FOXP3 (e.g., to abrogate the activity/kill $CD4^+/CD25^+$ Treg cells); Flt3 ligand, imiquimod (Aldara™), TLR agonists, including but not limited to TLR-2 agonists, TLR-4 agonists, TLR-7 agonists, and TLR-9 agonists; TLR antagonists, including but not limited to TLR-2 antagonists, TLR-4 antagonists, TLR-7 antagonists, and TLR-9 antagonists; anti-inflammatory agents and immunomodulators, including but not limited to, COX-2 inhibitors (e.g., Celecoxib, NSAIDS), glucocorticoids, statins, and thalidomide and analogs thereof including IMiDs® (which are structural and functional analogues of thalidomide (e.g., REVLIMID® (lenalidomide), POMALYST® (pomalidomide)) and any agents that modulate the number of, modulate the activation state of, and/or modulate the survival of antigen-presenting cells or of Th17, Th1, and/or Treg cells. Any combination of such agents is contemplated by the invention, and any of such agents combined with or administered in a protocol with (e.g., concurrently, sequentially, or in other formats with) a yeast-based immunotherapeutic is a composition encompassed by the invention. Such agents are well known in the art. These agents may be used alone or in combination with other agents described herein. In addition, one or more therapies can be administered or performed prior to the first dose of yeast-based immunotherapy composition or after the first dose is administered.

In aspects of the invention, an immunotherapeutic composition and other agents can be administered together (concurrently). As used herein, concurrent use does not necessarily mean that all doses of all compounds are administered on the same day at the same time. Rather, concurrent use means that each of the therapy components (e.g., immunotherapy and anti-viral therapy) are started at approximately the same period (within hours, or up to 1-7 days of each other) and are administered over the same general period of time, noting that each component may have a different dosing schedule (e.g., immunotherapy monthly, anti-viral daily). In addition, before or after the concurrent administration period, any one of the agents or immunotherapeutic compositions can be administered without the other agent(s).

In the method of the present invention, compositions and therapeutic compositions can be administered to animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Mammals to treat or protect include humans, dogs, cats, mice, rats, goats, sheep, cattle, horses and pigs.

An "individual" is a vertebrate, such as a mammal, including without limitation a human. Mammals include, but are not limited to, farm animals, sport animals, pets, primates, mice and rats. The term "individual" can be used interchangeably with the term "animal", "subject" or "patient".

General Techniques Useful in the Invention

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); *Methods in yeast genetics: a laboratory course manual*, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); Current Protocols in Molecular Biology (F. M. Ausubel et al., eds., 1987, including supplements through 2001); *PCR: The Polymerase Chain Reaction*, (Mullis et al., eds., 1994); Harlow and Lane (1988), *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000); Casarett and Doull's *Toxicology The Basic Science of Poisons*, C. Klaassen, ed., 6th edition (2001), and *Vaccines*, S. Plotkin and W. Orenstein, eds., 3rd edition (1999).

General Definitions

A "TARMOGEN®" (GlobeImmune, Inc., Louisville, Colo.) generally refers to a yeast vehicle expressing one or more heterologous antigens extracellularly (on its surface), intracellularly (internally or cytosolically) or both extracellularly and intracellularly. TARMOGEN® products have been generally described (see, e.g., U.S. Pat. No. 5,830,463). Certain yeast-based immunotherapy compositions, and methods of making and generally using the same, are also described in detail, for example, in U.S. Pat. Nos. 5,830,463, 7,083,787, 7,736,642, Stubbs et al., *Nat. Med.* 7:625-629 (2001), Lu et al., *Cancer Research* 64:5084-5088 (2004), and in Bernstein et al., *Vaccine* 2008 Jan. 24; 26(4):509-21, each of which is incorporated herein by reference in its entirety.

As used herein, the term "analog" refers to a chemical compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but has a different structure or origin with respect to the reference compound.

The terms "substituted", "substituted derivative" and "derivative", when used to describe a compound, means that at least one hydrogen bound to the unsubstituted compound is replaced with a different atom or a chemical moiety.

Although a derivative has a similar physical structure to the parent compound, the derivative may have different chemical and/or biological properties than the parent compound. Such properties can include, but are not limited to, increased or decreased activity of the parent compound, new activity as compared to the parent compound, enhanced or decreased bioavailability, enhanced or decreased efficacy, enhanced or decreased stability in vitro and/or in vivo, and/or enhanced or decreased absorption properties.

In general, the term "biologically active" indicates that a compound (including a protein or peptide) has at least one detectable activity that has an effect on the metabolic or other processes of a cell or organism, as measured or observed in vivo (i.e., in a natural physiological environment) or in vitro (i.e., under laboratory conditions).

According to the present invention, the term "modulate" can be used interchangeably with "regulate" and refers generally to upregulation or downregulation of a particular activity. As used herein, the term "upregulate" can be used generally to describe any of: elicitation, initiation, increasing, augmenting, boosting, improving, enhancing, amplifying, promoting, or providing, with respect to a particular activity. Similarly, the term "downregulate" can be used generally to describe any of: decreasing, reducing, inhibiting, ameliorating, diminishing, lessening, blocking, or preventing, with respect to a particular activity.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA, immunoblot assays, etc.).

Reference to a protein or polypeptide used in the present invention includes full-length proteins, fusion proteins, or any fragment, domain, conformational epitope, or homologue of such proteins, including functional domains and immunological domains of proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have enhanced, decreased, or substantially similar properties as compared to the naturally occurring protein or peptide. A homologue can include an agonist of a protein or an antagonist of a protein. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

A homologue of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 91% identical, or at least about 92% identical, or at least about 93% identical, or at least about 94% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

A homologue may include proteins or domains of proteins that are "near full-length", which means that such a homologue differs from the full-length protein, functional domain or immunological domain (as such protein, functional domain or immunological domain is described herein or otherwise known or described in a publicly available sequence) by the addition of or deletion of 1, 2, 3, 4, 5, 6, 7, 8, 9, or 10 amino acids from the N- and/or the C-terminus of such full-length protein or full-length functional domain or full-length immunological domain.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schaaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174:247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors. Preferred recombinant vectors are capable of being expressed in a transfected host cell.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

Example 1

The following Example shows that responders in a pancreatic cancer clinical study treated with a yeast immunotherapy expressing mutated Ras were either sensitive or resistant to type 1 interferon (T1IFN), which correlated with outcome.

Measuring T1IFN Sensitivity Using Human Subject Clinical Samples:

Signaling emanating from a T1IFN ligand initiates the activation of transcription factors that activate or repress T1IFN regulated genes that encode effector proteins. The present inventors adapted an approach developed by Feng et al., 2012, supra to measure the T1IFN induced M×A protein. More particularly, the present inventors first developed the assay using PBMCs from healthy volunteers in order to confirm that the M×A protein signal did not erode when samples were frozen and thawed, since the Feng et al. analyses were performed from freshly isolated PBMCs. By assaying each individual rather than pooling blood samples, it was observed that subjects had different sensitivities to T1IFN which fell along a continuum. The question asked was whether T1IFN-sensitivity could be used to discriminate between those with good and poor outcomes in a Phase 2 pancreatic cancer immunotherapy trial.

In the Phase 2 clinical study for patients with resected pancreas cancer, patients (n=176) were enrolled in two arms at 27 centers globally. The study drug was a yeast-based immunotherapeutic (TARMOGEN® product, GlobeImmune, Inc., Louisville, Colo.) known as GI-4000. GI-4000 is a series of yeast-based immunotherapy products developed by GlobeImmune, Inc. that target mutated Ras. GI-4000 currently consists of four different heat-inactivated *S. cerevisiae* yeast (referred to individually as "GI-4014", "GI-4015", "GI-4016" and "GI-4020"), together expressing seven common Ras mutations in human cancers. Each protein product expressed in the yeast contains: (A) two mutations at codon 61 (glutamine to arginine [Q61R] (GI-4014, GI-4015, GI-4016) or glutamine to histidine [Q61H] (GI-4020), and glutamine to leucine [Q61L] (GI-4014, GI-4015, GI-4016, GI-4020); plus (B) one of four different mutations at codon 12 (glycine to valine [G12V] (GI-4014), glycine to cysteine [G12C] (GI-4015), glycine to aspartate [G12D] (GI-4016), or glycine to arginine [G12R] (GI-4020)). Patient tumors were sequenced to identify the specific Ras mutation(s) contained in their tumor, and only the specific yeast immunotherapeutic with the matching mutation was administered to the patient.

Patients were administered GlobeImmune's GI-4000 product matched to their Ras mutation(s) at 40 Y.U., or with placebo using three weekly doses starting between 21 and 35 days after resection (study visit Day 1, 8, 15), and all subjects received gemcitabine (GEM) 1000 mg/$m^2$ by intravenous infusion starting on study visit Day 24. Administration of GEM proceeded until either six monthly cycles were completed, GEM intolerance, study withdrawal, disease progression, or death occurred. Administration of study drug (GI-4000) proceeded until study withdrawal, disease recurrence, or death and could proceed beyond GEM cessation. Immune samples were collected from subjects on select study visits: Day 1 (baseline), 15, 24, 44, 52, 100, 108, 184 and then quarterly during on treatment and post study drug follow up phase.

As discussed previously herein, a restrospective proteomic analysis using a potential proteomic companion diagnostic test (BDX-001; Biodesix, Inc., Boulder, Colo.) appeared to predict whether a subset of subjects treated with GI-4000 and gemcitabine in this trial would have improved recurrence free survival (RFS) and overall survival (OS) compared to subjects treated with placebo plus gemcitabine. (Richards et al., 2012, *European Society for Medical Oncology* (*ESMO*); Richards et al., 2014, *American Association for Cancer Research* (*AACR*)).

In the pilot experiments conducted in the present invention, 14 subject samples from the GI-4000 clinical study were tested: seven samples from subjects who had a more favorable clinical outcome, measured in terms of longer overall survival (OS) and/or longer recurrence free survival (RFS)), and seven samples from subjects who had a less favorable clinical outcome, measured in terms of shorter overall survival (OS) and/or shorter recurrence free survival (RFS). The first seven samples were also previously characterized as "BDX-001 positive" and the second seven samples were previously characterized as "BDX-001 negative", although the goal of the current experiment was to determine generally whether there is a correlation between T1IFN-sensitivity and clinical outcome, regardless of BDX-001 status. These subjects were selected for the analyses from their banked samples based on the fact that they had the most abundant frozen samples available at time 0 taken prior to treatment. FIG. 1 is a Western blot from six of the 13 patient PBMC samples (one sample provided no signal). Each subject is defined by ratio (the scan quantification of M×A protein after T1IFN addition versus before T1IFN addition). Each sample was run in duplicate without (0) and with (160 U/mL) of IFN-β (this concentration of IFN-β was optimized in prior studies to achieve the highest level of M×A production, data not shown). The first subject, designated 0132 CLB, had an M×A ratio of 0.87, meaning an unchanged M×A protein before versus after addition of T1IFN. For the purpose of this analysis, this person was classified as T1IFN resistant since M×A protein was unaffected by addition of T1IFN.

More specifically, FIG. 1 shows that T1IFN-sensitivity associates with a positive outcome following whole yeast based immunotherapy. Samples from six subjects treated with yeast-based immunotherapy collected prior to treatment initiation were tested for T1IFN sensitivity/insensitivity defined by measuring the T1IFN response gene product M×A in PBMCs prior to and after the addition of T1IFN in vitro. FIG. 1 shows six subjects identified as 0132, 0508, 0539, 0532, 0526 and 0125. PBMCs were placed in culture with or without the addition of 160 U/mL of IFN-β. Each sample was run in duplicate. By comparing the scanned gel signal and generating a ratio of signal before versus after T1IFN treatment, the data show that for subjects denoted 0132, 0508 and 0125, the ratios are 0.87, 1.3 and 2.4 and for subjects 0539, 0532 and 0526, the ratios are 6.3, 5.9 and 7.6.

The Western blot data categorizes subjects 539, 532 and 526 as sensitive to T1IFN defined by substantial increase in M×A protein levels after T1IFN induction, while subjects 132, 508 and 126 can be deemed to be insensitive, or at least less sensitive to T1IFN (e.g., subjects 0508 and 0125 did have some responsiveness to T1IFN, although this was low enough to be considered as T1IFN-insensitive in this assay). Those subjects classified by Western blot as sensitive to T1IFN had RFS following treatment initiation of >500 days (695, 642, 562 days, respectively). Those with the "T1IFN-insensitive" Western blot signal had an RFS <500 days (354, 275, 290 days, respectively).

In the total 13 subject cohort, all seven of the subjects deemed long term survivors according to overall survival (OS) and recurrence free survival (RFS) were considered T1IFN-sensitive by the M×A assay. All of these subjects had ratios of M×A protein of greater than 5 (actual ratios were: 46.6, 27.2, 14.2, 10.1, 7.6, 6.3, and 5.9.) Of the six subjects who were shorter term survivors according to OS and RFS, three out of four subjects had clearly unchanged ratios (1.3, 0.9, 0.9), and the fourth subject had a ratio of 2.4. Two subjects, however, had ratios of 14.6 and 9.0. In the T1IFN analyses that were performed initially on healthy volunteers, four subjects were T1IFN-sensitive and six were T1IFN-insensitive. Taken together, this preliminary data subset indicates, at minimum, that the PBMC T1IFN sensitivity assay can predict those subjects who are most likely to respond to yeast-based immunotherapy by T1IFN-sensitivity, and those subjects having a T1IFN-insensitivity signal are trending towards a poor outcome.

Figure 2:
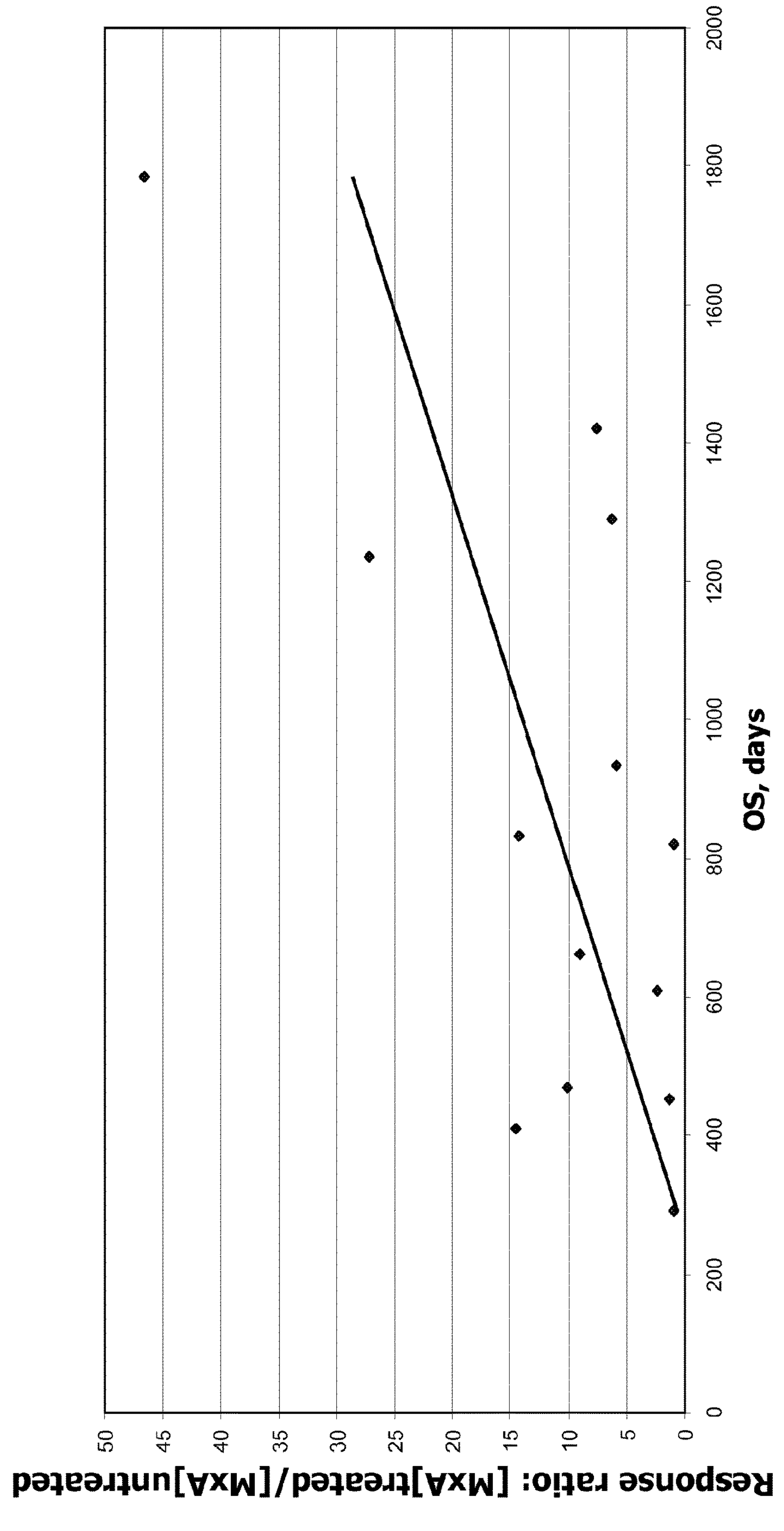
FIG. 2 is a graph showing that in a cohort of 13 cancer patients who received a yeast-based immunotherapy composition known as GI-4000, T1IFN-responsiveness correlated in a statistically significant manner with overall survival (OS).
Figure 3:
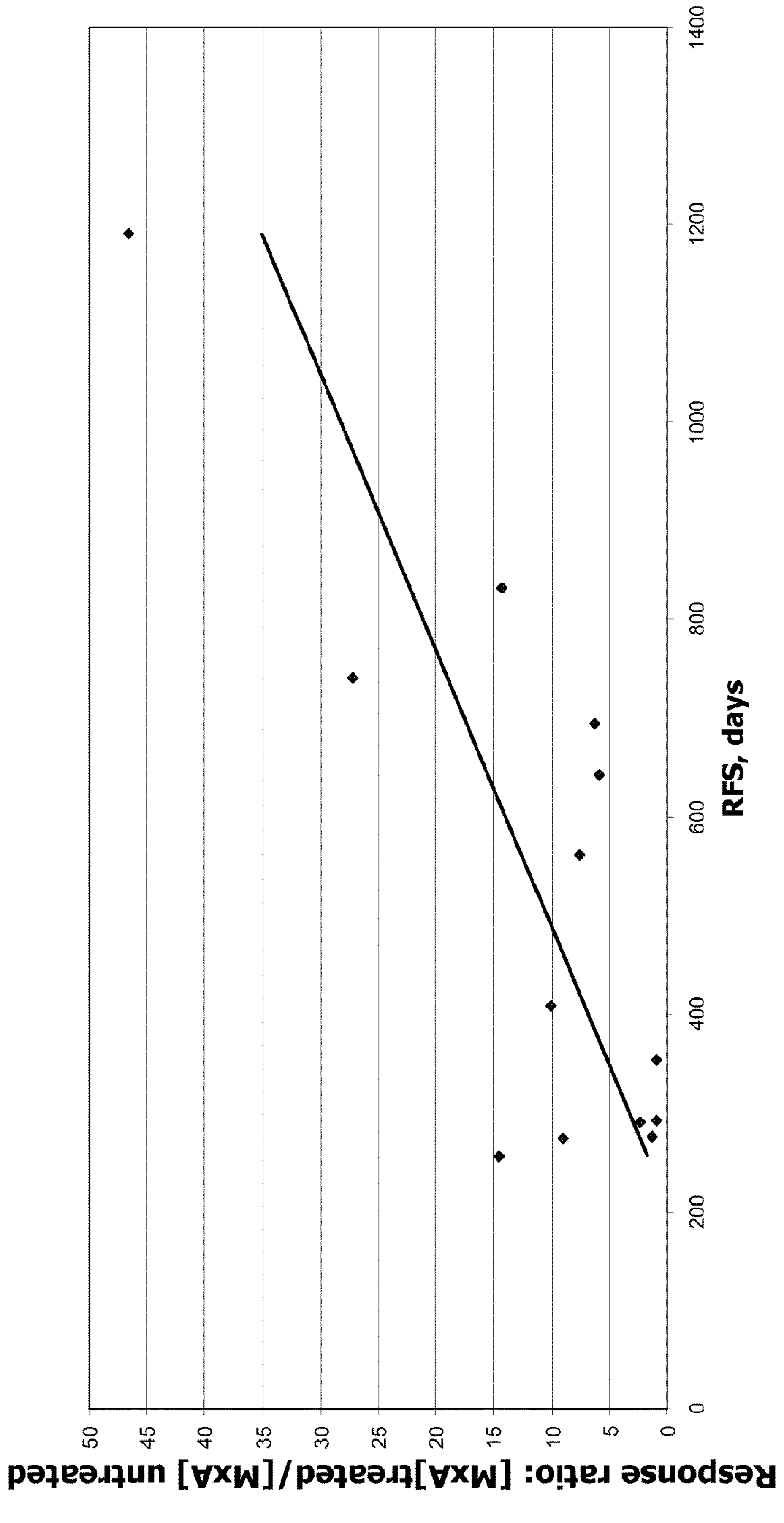
FIG. 3 is a graph showing that in a cohort of 13 cancer patients who received a yeast-based immunotherapy composition known as GI-4000, T1IFN-responsiveness correlated in a statistically significant manner with recurrence free survival (RFS).

In an additional analysis, the results being shown in FIGS. 2 and 3, PBMCs from patients treated with GI-4000 were thawed, washed, and counted, and the cells were adjusted to a density of 0.5×$10^7$ cells/mL in RPMI. A T1IFN response was induced for 24 h with 160 U/mL IFN-β (control=no induction). Cells were harvested and lysates were prepared by sonication in standard mammalian cell lysis buffer containing protease inhibitors and sodium orthovanadate to prevent phosphatase activity. Total protein analysis was conducted by heating samples at 95° C. for 5 min, and loading SDS-PAGE gels for Western blot analysis (equal total protein loading/lane). Western blots were probed with anti-M×A antibody and M×A protein was quantified using enhanced chemiluminescence digital imaging. Data was analyzed as the ratio of TI1FN-induced/uninduced band intensities. Correlation and associated p values was performed by external vendor (Dr. Stan Deming, Statistical Designs, Houston, Tex.).

As shown in FIGS. 2 and 3, survival and T1IFN response were correlated for GI-4000-treated pancreas cancer patients with patients receiving GI-4000 and identified as T1IFN-sensitive having an improved overall survival (OS; FIG. 2; correlation coefficient 0.6585; p=0.0144; confidence 98.6%)) and recurrence free survival (RFS; FIG. 3; correlation coefficient 0.7905; p=0.0013; confidence 99.87%)) as compared to patients receiving GI-4000 and identified as T1IFN-resistant. The results were statistically significant.

Accordingly, yeast-based immunotherapy responsiveness is positively correlated with sensitivity to type 1 interferons, which can now be used to pre-select individuals who are the most likely to respond to yeast-based immunotherapy in a clinically meaningful/beneficial manner.

Example 2

The following Example provides additional evidence that T1IFN-sensitivity correlates with overall survival and recurrence free survival in a statistically significant manner in subjects treated with yeast-based immunotherapy.

In this example, in order to examine the relationship between T1IFN-sensitivity and clinical outcome in a larger cohort of subjects, the T1IFN response of GI-4000 pancreas cancer subjects was again determined in pre-treatment (baseline) PBMC samples, using those subject samples described in Example 1 above, as well as additional samples from other GI-4000-treated subjects (i.e., subjects receiving the yeast-based immunotherapy known as GI-4000 plus gemcitabine) from the same clinical study. In addition, samples from a cohort of subjects from the same clinical study who were treated with placebo (i.e., placebo plus gemcitabine) were tested to determine whether T1IFN-sensitivity correlated with clinical outcome in these patients (i.e., to determine whether or not the effect was associated with yeast-based immunotherapy).

More particularly, PBMCs were thawed and washed in complete RPMI medium containing 10% fetal bovine serum (cRPMI-10). Five million viable cells were resuspended in 2 mL cRPMI and the suspension was divided into 2 wells of a 24 well plate (1 mL per well). IFN-β was added to a final concentration of 160 U/mL for one of the wells and medium alone (mock treatment) was added to the other. After a 24 h incubation at 37° C., the cells were harvested for 6 minutes at 300×g and cell pellets were lysed in ice cold RIPA buffer containing 1 mM sodium orthovanadate and a protease inhibitor cocktail, plus 1× SDS-PAGE gel loading buffer. Samples were sonicated for 15 seconds (1 second pulses separated by 1 second). The samples were then heated to 95° C. for 5 minutes, and the total protein concentration was determined using a dye binding method (Schaffner et al., 1973, *Anal Biochem* 56:502-514). Western blot analysis of M×A expression was conducted per established enhanced chemiluminescence methods. Digital imaging of banding intensities was used to quantify M×A expression level.

Figure 4A:
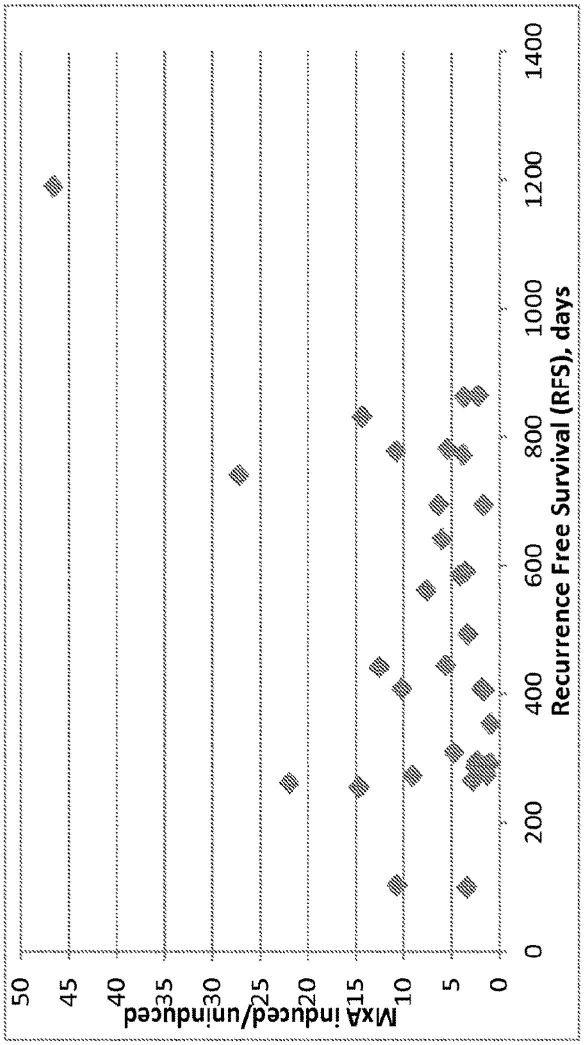
FIG. 4A is a graph showing that T1IFN-sensitivity correlates with recurrence free survival (RFS) in a statistically significant manner in pancreas cancer patients treated with GI-4000 and gemcitabine.
Figure 4B:
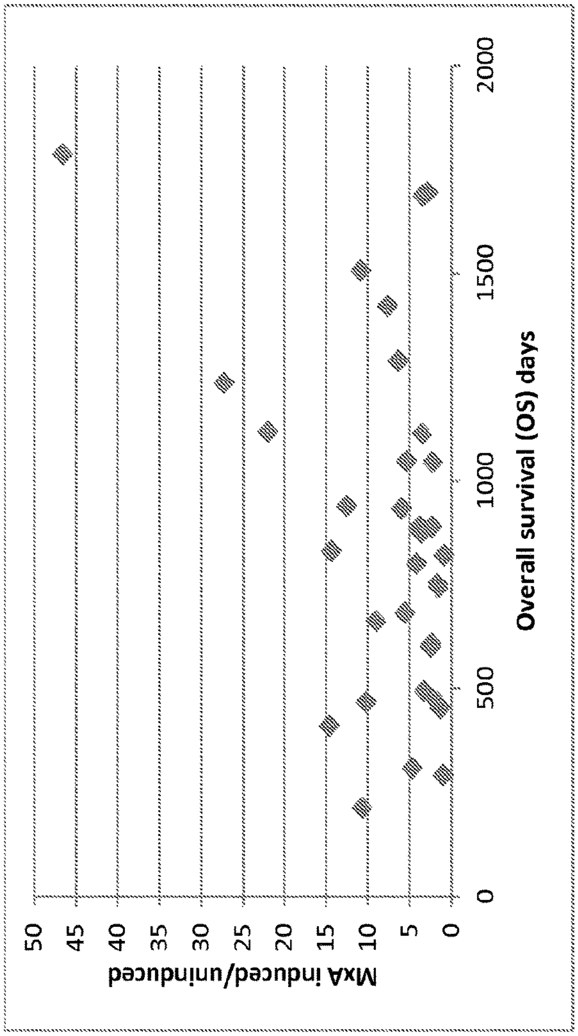
FIG. 4B is a graph showing that T1IFN-sensitivity correlates with overall survival (OS) in a statistically significant manner in pancreas cancer patients treated with GI-4000 and gemcitabine.
Figure 5A:
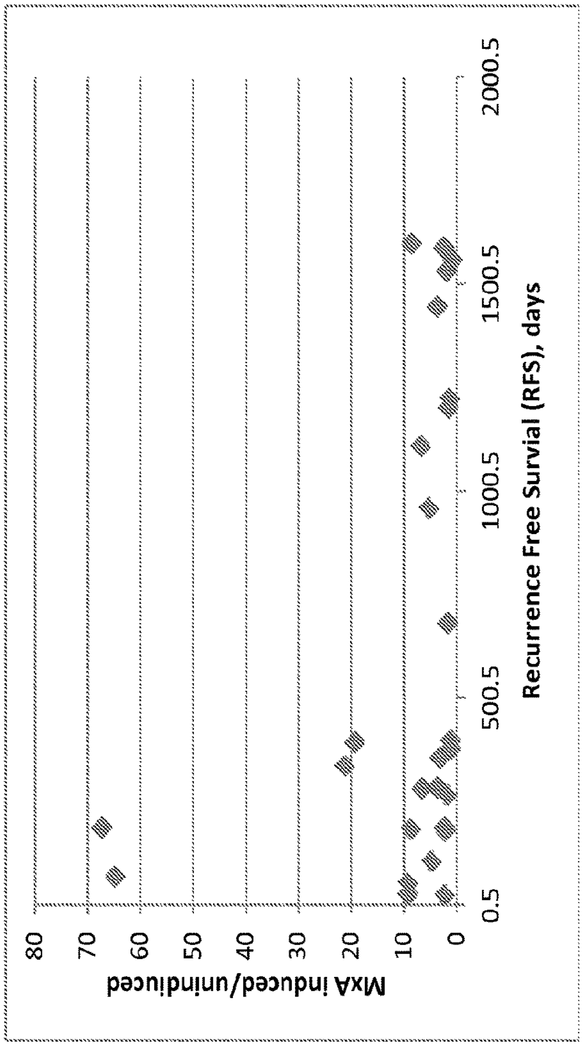
FIG. 5A is a graph showing that in pancreas cancer patients treated with placebo and gemcitabine, T1IFN-sensitivity did not correlate with RFS.
Figure 5B:
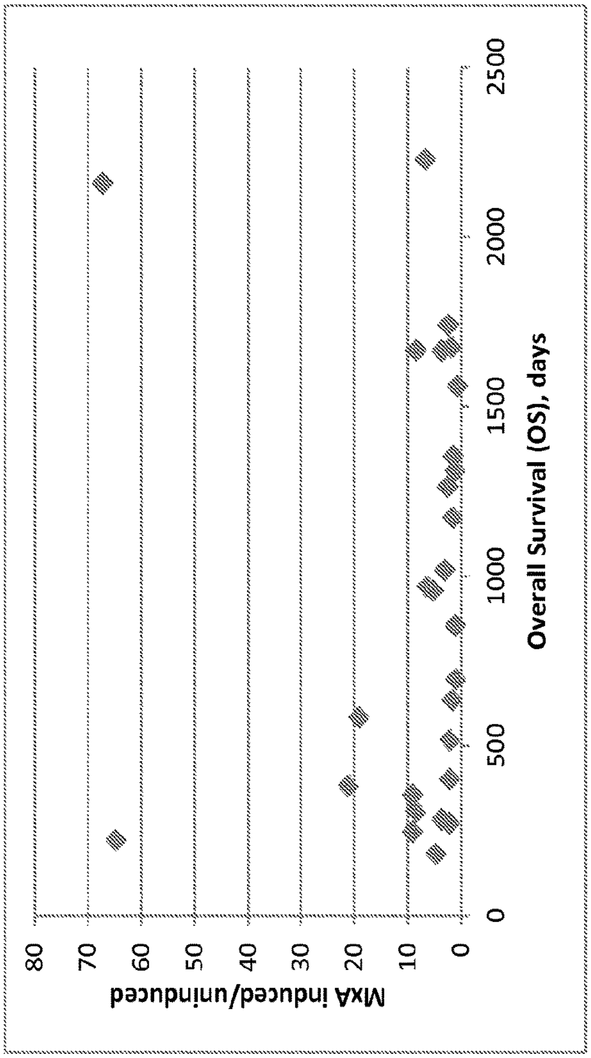
FIG. 5B is a graph showing that in pancreas cancer patients treated with placebo and gemcitabine, T1IFN-sensitivity did not correlate with OS.

T1IFN induced/uninduced M×A ratios for each subject were calculated and correlation coefficients and p values were determined for M×A vs. recurrence free survival (RFS) (FIG. 4A for GI-4000-treated subjects and FIG. 5A for placebo-treated subjects) or M×A vs. overall survival (OS) (FIG. 4B for GI-4000-treated subjects and FIG. 5B for placebo-treated subjects). As another level of analysis, subjects were additionally categorized into various subgroups, those with an M×A ratio (i.e., ratio of M×A level post-IFN-β-exposure to the M×A level pre-IFN-β-exposure) <3 or ≥3 (FIG. 6A for GI-4000-treated subjects and FIG. 7A for placebo-treated subjects) and those with an M×A ration of <5 or ≥5 (FIG. 6B for GI-4000-treated subjects and FIG. 7B for placebo-treated subjects), and survival time was plotted for each group as a scatter graph.

The results shown in FIGS. 4A and 4B indicate that the survival time of GI-4000-treated subjects (FIG. 4A RFS and FIG. 4B OS) correlates with the magnitude of the in vitro T1IFN response in baseline PBMC samples. For these subjects, the correlation coefficient for RFS vs. baseline M×A response was +0.4179 (p=0.0155) and the correlation coefficient for OS vs. baseline M×A response was +0.3925 (p=0.0239). As shown in FIG. 5A (placebo-treated subjects RFS) and FIG. 5B (placebo-treated subjects OS), statistically significant correlations were not observed in these samples (for RFS, FIG. 5A, correlation coefficient was −0.2474, p=0.1957 and for FIG. 5B, correlation coefficient was −0.0942, p=0.63). Therefore, T1IFN-sensitivity correlates with survival (RFS and OS) in subjects treated with yeast-based immunotherapy in a statistically significant manner, while this biomarker did not correlate with survival in subjects who received placebo (i.e., the T1IFN biomarker is a predictor of outcome for yeast-based immunotherapy).

Figure 6B:
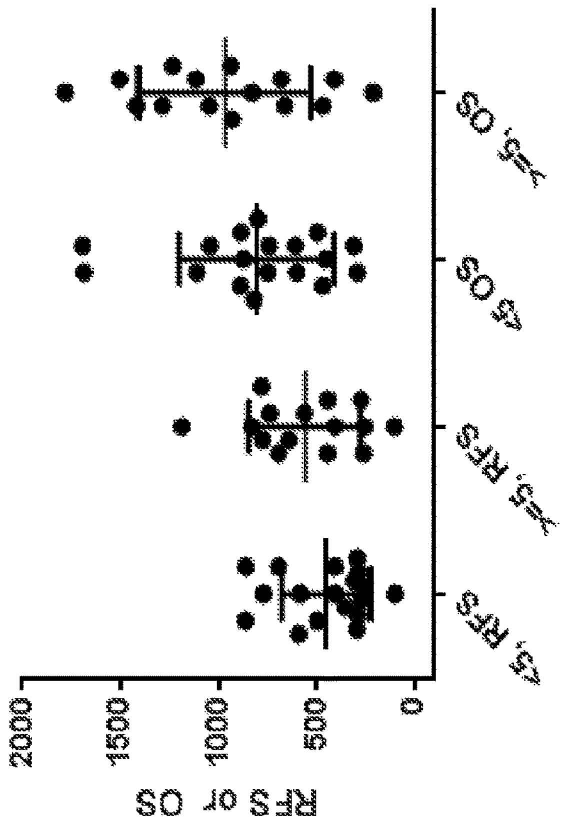
FIG. 6B is a graph showing that T1IFN-sensitivity trends in a correlative manner with improved survival (RFS and OS) of GI-4000-treated (GI-4000+gemcitabine) pancreas cancer patients with a T1 IFN biomarker ratio of greater than 5.
Figure 6A:
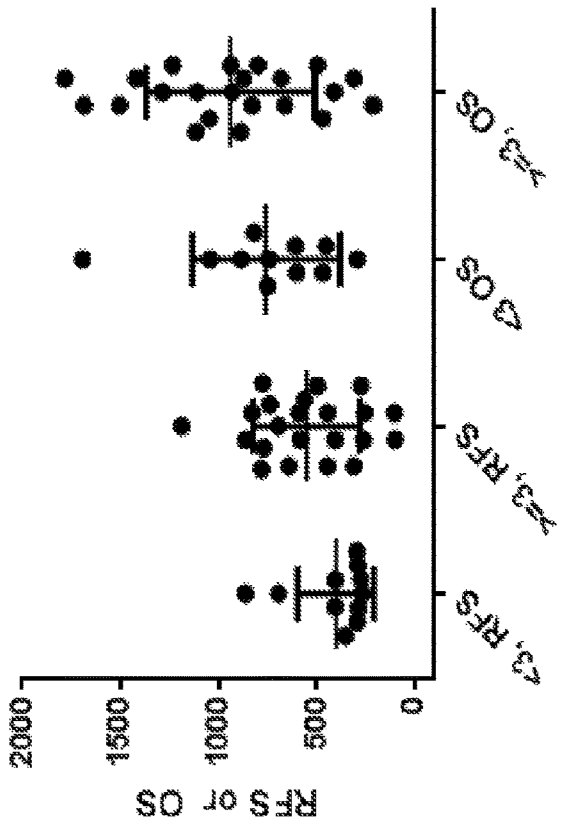
FIG. 6A is a graph showing that T1IFN-sensitivity trends in a correlative manner with improved survival (RFS and OS) of GI-4000-treated (GI-4000+gemcitabine) pancreas cancer patients with a T1IFN biomarker ratio of greater than 3.
Figure 7B:
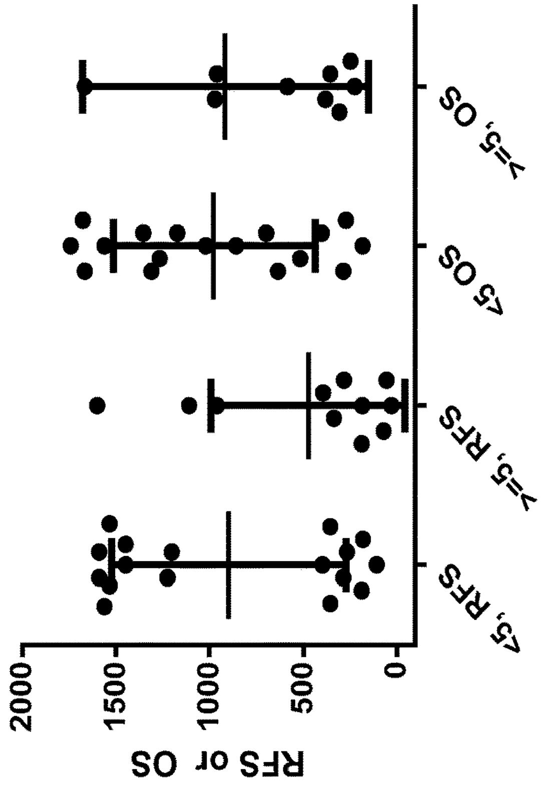
FIG. 7B is a graph showing that T1IFN-sensitivity does not trend in a correlative manner with survival (RFS and OS) of placebo-treated (placebo+gemcitabine)-treated pancreas cancer patients (T1IFN biomarker ratio cutoff set at 5).
Figure 7A:
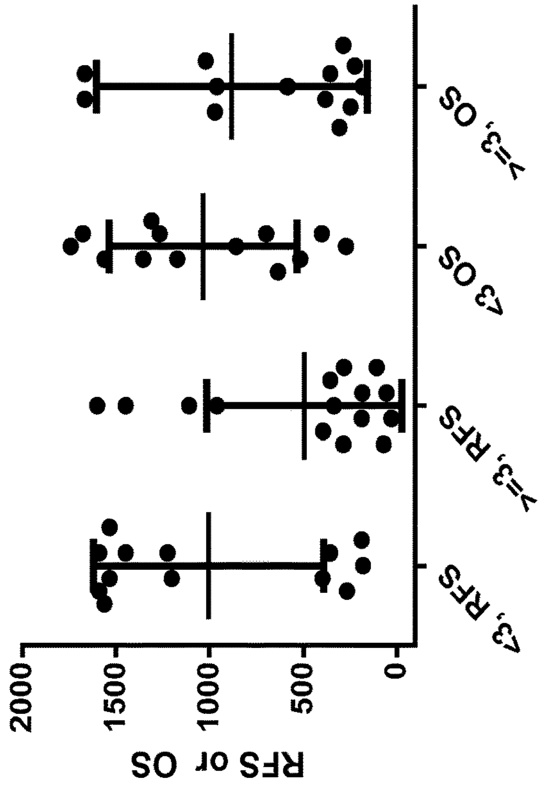
FIG. 7A is a graph showing that T1IFN-sensitivity does not trend in a correlative manner with improved survival (RFS and OS) of placebo-treated (placebo+gemcitabine)-treated pancreas cancer patients (T1IFN biomarker ratio cutoff set at 3).

The results of the categorical response measure (M×A cutoff values of 3 or 5) also indicate that a positive relationship exists between T1IFN-sensitivity and survival, where the average survival time (RFS and OS) was longer for GI-4000-treated subjects having M×A ratios ≥3 than for subjects whose M×A ratio was <3 (FIG. 6A). A similar conclusion was reached when a M×A ratio cutoff of 5 was used (FIG. 6B). These relationships were not observed for the placebo arm (FIGS. 7A and 7B) and in fact, survival time was actually somewhat reduced for subjects with M×A ratios ≥3 or ≥5 (FIG. 7A). Accordingly, these results also indicate that a positive relationship between T1IFN-sensitivity and clinical outcome was observed in subjects treated with yeast-based immunotherapy grouped by categorical response, but not in subjects treated with placebo.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to treat a subject having a cancer selected from the group consisting of pancreatic cancer, colorectal cancer, lung cancer, melanoma, and leukemia, and who is sensitive to Type-1 Interferon with yeast-based immunotherapy, comprising:

a) preselecting a subject who is sensitive to Type 1 Interferon comprising the steps of:
   i) measuring a baseline level of one or more Type 1 Interferon-regulated biomarkers ex vivo or in vitro in a biological sample isolated from the subject;
   ii) contacting the biological sample with Type 1 Interferon;
   iii) measuring the level of the one or more Type 1 Interferon-regulated biomarkers after step (ii) of contacting; and
   iv) preselecting Type 1 Interferon-sensitive subjects for treatment with yeast-based immunotherapy whose level of the one or more Type 1 Interferon-regulated biomarker is up- or down-regulated at least three-fold as a result of contacting the biological sample with Type 1 Interferon; and b) administering yeast-based immunotherapy to the subject, wherein the yeast-based immunotherapy is administration of a whole yeast that has recombinantly expressed one or more cancer antigens.

2. The method of claim 1, wherein the step (i) and/or (iii) of measuring comprises using an assay selected from the group consisting of: enzyme-linked immunosorbant assay, real-time polymerase chain reaction, flow cytometry, multiplex bead-based immunoassay, and quantitative selected reaction monitoring based mass spectrometry.

3. The method of claim 1, wherein subjects are preselected whose level of the one or more T1IFN-regulated biomarker was up- or down-regulated at least five-fold from the baseline level as a result of contacting the biological sample with Type 1 Interferon.

4. The method of claim 1, wherein the step (a) of preselecting further comprises the steps of:

further contacting the biological sample with Type 1 Interferon after step (iii) and measuring the level of the one or more Type 1 Interferon-regulated biomarkers after contacting the biological sample with Type 1 Interferon after step (iii); and preselecting Type 1 Interferon-sensitive subjects for treatment with yeast-based immunotherapy whose level of the one or more Type 1 Interferon-regulated biomarker was up- or down-regulated at least three fold as a result of contacting the biological sample with Type 1 Interferon in step (ii), and whose level of the one or more Type 1 Interferon-regulated biomarker was not up or down-regulated as a result of further contacting the biological sample with Type 1 Interferon.

5. The method of claim 1, wherein the biological sample has not been exposed to exogenous Type 1 Interferon prior to preselecting the subject.

6. The method of claim 1, wherein the subject has not received an exogenous source of Type 1 Interferon prior to step (a).

7. The method of claim 1, wherein the biological sample is peripheral blood mononuclear cells or a tissue biopsy from the subject.

8. The method of claim 1, wherein cells in the biological sample upregulate one or more type 1 interferon-stimulated genes (ISGs) as a result of contact with Type 1 Interferon ex vivo or in vitro.

9. The method of claim 1, wherein a Type 1 Interferon-regulated biomarker in the biological sample has increased phosphorylation as a result of contact with Type 1 Interferon ex vivo or in vitro.

10. The method of claim 1, wherein cells in the biological sample produce a higher level of Type 1 Interferon-regulated protein as a result of contact with Type 1 Interferon ex vivo or in vitro.

11. The method of claim 1, wherein the Type 1 Interferon is interferon-α or interferon β.

12. The method of claim 1, wherein the subject has cancer or an infectious disease.

* * * * *

UNITED STATES PATENT AND TRADEMARK OFFICE

CERTIFICATE OF CORRECTION

PATENT NO. : 10,799,567 B2
APPLICATION NO. : 15/303434
DATED : October 13, 2020
INVENTOR(S) : Bellgrau et al.

It is certified that error appears in the above-identified patent and that said Letters Patent is hereby corrected as shown below:

On the Title Page

Item (71), please delete "THE REGENTS OF THE UNIVERSITY OF COLORADO, Denver, CO (US)" and insert -- THE REGENTS OF THE UNIVERSITY OF COLORADO, A BODY CORPORATE, Denver, CO (US) --

Item (73), please delete "The Regents of the University of Coloradio, Denver, CO (US)" and insert -- The Regents of the University of Colorado, a Body Corporate, Denver, CO (US) --

Signed and Sealed this
Nineteenth Day of January, 2021

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: synthetic peptide

<400> SEQUENCE: 1

Met Ala Asp Glu Ala Pro
1               5
```